United States Patent
Tunge et al.

(10) Patent No.: US 8,921,486 B2
(45) Date of Patent: Dec. 30, 2014

(54) POLYMER-SUPPORTED TRANSITION METAL CATALYST COMPLEXES AND METHODS OF USE

(75) Inventors: Jon Tunge, Lawrence, KS (US); Bala Subramaniam, Lawrence, KS (US); Jing Fang, Lawrence, KS (US); Ranjan Jana, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 207 days.

(21) Appl. No.: 13/128,990

(22) PCT Filed: Nov. 16, 2009

(86) PCT No.: PCT/US2009/064595
§ 371 (c)(1),
(2), (4) Date: May 12, 2011

(87) PCT Pub. No.: WO2010/057099
PCT Pub. Date: May 20, 2010

(65) Prior Publication Data
US 2011/0230620 A1   Sep. 22, 2011

Related U.S. Application Data

(60) Provisional application No. 61/114,716, filed on Nov. 14, 2008, provisional application No. 61/143,538, filed on Jan. 9, 2009.

(51) Int. Cl.
| | | |
|---|---|---|
| C08K 5/07 | (2006.01) | |
| B01J 31/16 | (2006.01) | |
| B01J 31/18 | (2006.01) | |
| B01J 31/24 | (2006.01) | |

(52) U.S. Cl.
CPC ............ *B01J 31/1658* (2013.01); *B01J 31/185* (2013.01); *B01J 31/2404* (2013.01); *B01J 2231/321* (2013.01); *B01J 2231/344* (2013.01); *B01J 2531/0238* (2013.01); *B01J 2531/822* (2013.01)
USPC .......................................... 525/153; 525/154

(58) Field of Classification Search
USPC ............... 504/159, 166, 171; 548/403; 546/2; 525/153, 333.3, 154, 319; 568/454; 260/429; 502/115, 159
See application file for complete search history.

(56) References Cited

U.S. PATENT DOCUMENTS

| | | | |
|---|---|---|---|
| 5,298,669 | A | 3/1994 | Healy et al. |
| 5,817,883 | A | 10/1998 | Briggs et al. |
| 7,365,234 | B2 | 4/2008 | Subramanian et al. |
| 2003/0130113 | A1* | 7/2003 | Schmid et al. ................ 502/167 |
| 2005/0038289 | A1 | 2/2005 | Gordon et al. |
| 2006/0074206 | A1 | 4/2006 | Lipian |

FOREIGN PATENT DOCUMENTS

| | | | |
|---|---|---|---|
| GB | WO0168726 | * | 9/2001 |
| JP | 2002-516891 | | 6/2002 |

OTHER PUBLICATIONS

Jongsma et al., A new type of highly active polymer-bound rhodium hydroformylation catalyst, polymer, 1992, vol. 33, pp. 161-165.*
Derwent 1996-186819, Aug. 1995, RU, Musina.*
Shibahara et al., Solvent-Free Asymmetric Olefin Hydroformylation Catalyzed by Highly Cross-linked Polystyrene-Supported (R,S)-Binaphos-Rh(I) Complex, 2003, JACS,125, 8555-8560.*
Imyanitov, *Synthesis of high-molecular-weight phosphine ligands for catalysts of homogeneous reactions*, Neftekhiiia 32(3) 200-207 (1992).
Jongsma et al., *A new type of highly active polymer-bound rhodium hydroformylation catalyst*, Polymer 33(1) 161-165 (1992).
Bergbreiter, *Using Soluble Polymers to Recover Catalysts and Ligands*, Chem Rev 102 3345-3384 (2002).
Bergbreiter, *Using Soluble Polymers to Recover Catalysts and Ligands*, Chem. Rev. 102 3345-3384 (2002).
Fang, *Towards a Benign and Viable Rhodium Catalyzed Hydroformylation of Higher Olefins: Economic and Environmental Impact analyses, Solvent Effects and Membrane-based Catalyst Separation*, Dissertation, Apr. 10, 2009.
M.E. Wilson et al., Conversion of a Protein to a Homogeneous Asymmetric Hydrogenation Catalyst by Site-Specific Modification with a Diphosphinerhodium (I) Moiety, J. Am. Chem. Soc., vol. 100, pp. 306-307 (1978).
A.V. Malkov et al., Soluble Polymer-Supported Organocatalysts: Asymmetric Reduction of Imines with Trichlorosilane Catalyzed by an Amino Acid Derived Formamide Anchored to a Soluble Polymer, Chem. Eur. J., vol. 15, pp. 9651-9654 (2009), Published online: Aug. 26, 2009.

\* cited by examiner

*Primary Examiner* — Monique Peets
(74) *Attorney, Agent, or Firm* — Stinson Leonard Street LLP

(57) ABSTRACT

A catalyst composition comprising a polymer functionalized with a ligand for binding a transition metal containing compound to form a transition metal complex, wherein said functionalized polymer has a number average molecular weight of about 5,000 to 30,000 g/mol and a polydispersity index of about 1.0 to 2.0. The catalyst is used in a hydroformylation reaction, preferably one in which the liquid phase has been volumetrically expanded with a compressed gas, is readily recyclable using nanofiltration.

37 Claims, 9 Drawing Sheets

$^{31}$P NMR of PBB 10 (8)

$^{31}$P NMR for compound PBB 10 (8) after binding with Rh(acac)(CO)$_2$

POLYMER-SUPPORTED TRANSITION METAL CATALYST COMPLEXES AND METHODS OF USE

BACKGROUND OF THE INVENTION

The hydroformylation reaction is well known in the art as a catalytic method for the conversion of an olefin into an aldehyde product having one carbon more than the starting olefin by the addition of one molecule each of hydrogen and carbon monoxide to the carbon-carbon double bond. If the organic substrate contains more than one carbon-carbon double bond, more than one formyl group can be added to the substrate, thereby increasing the number of carbon atoms contained in the product molecule by more than one.

Industrial processes for the catalytic hydroformylation of higher olefins (i.e., those olefins having more than five carbons) face several challenges, including efficient catalyst recovery/recycle and the limited solubilities of the gaseous reactants ($H_2$ and CO) in the liquid reaction phase. See Frohling et al., *Applied homogeneous catalysis with organometallic compounds*, VCH, Weinheim, Germany, 27-104 (1996). The commercial catalysts used in the lower olefin processes, mostly rhodium-based, are not applied in higher olefin hydroformylation because of their instability at the temperatures required for product separation/distillation. Hence, while the less expensive cobalt-based catalysts are used, harsher conditions (140-200° C., 5-30 MPa) are often employed to activate and stabilize the catalysts. In addition, the catalyst recovery typically involves significant quantities of solvents, acids, and bases in a series of many operating units. See Garton et al., PCT International Application, WO 2003/082789. Thus, an engineered system is desired to realize process intensification at milder conditions with a highly active catalyst that requires a relatively simpler and environmentally friendlier catalyst recovery method. Similar issues and needs are encountered in carrying out other processes besides hydroformylation, for example, in hydrogenation, oxidation, and carbonylation.

Several approaches for catalyst recovery have been reported in literature. The first approach involves employing a "phase transition switch" whereby reactions are performed homogeneously, following which the catalysts are recovered from the product stream via phase transition triggered by a change in either the system temperature (see Horváth et al., *Facile catalyst separation without water: fluorous biphasic hydroformylation of olefins*, Science 266 (5182) 72-75 (1994); Zheng et al., *Thermoregulated phase transfer ligands and catalysis. III. Aqueous/organic two-phase hydroformylation of higher olefins by thermoregulated phase-transfer catalysis*, Catalysis Today 44 175-182 (1998)) or pressure (see Koch et al., *Rhodium-catalyzed hydroformylation in supercritical carbon dioxide*, Journal of American Chemical Society 120 13398-13404 (1998); Palo et al., *Effect of ligand modification on rhodium-catalyzed homogeneous hydroformylation in supercritical carbon dioxide*, Organometallics 19 81-86 (2000)).

The second approach involves biphasic media, such as water/organic (see Peng et al., Aqueous biphasic hydroformylation of higher olefins catalyzed by rhodium complexes with amphiphilic ligands of sulfonated triphenylphosphine analog, Catalysis Letters 88 219-225 (2003)), water/$CO_2$ (see Haumann et al., Hydroformylation in microemulsions: conversion of an internal long chain alkene into a linear aldehyde using a water soluble cobalt catalyst, Catalysis Today 79-80 43-49 (2003); McCarthy et al., Catalysis in inverted supercritical $CO_2$/aqueous biphasic media, Green Chemistry 4(5) 501-504 (2002)), and room temperature ionic liquid/$CO_2$ (see Webb, Continuous flow hydroformylation of alkenes in supercritical fluid-ionic liquid biphasic systems, Journal of American Chemical Society 125 15577-15588 (2003)), wherein the catalyst is sequestered in either the water or the ionic liquid phases whereas the product preferentially separates into the organic phase or the $CO_2$ phase.

The third approach involves immobilizing homogeneous rhodium ("Rh") catalysts on various supports to form a heterogenized catalyst that can be easily applied in fixed bed or slurry type reactors, i.e., the silicate MCM-41 (see Marteel et al., *Supported platinum/tin complexes as catalysts for hydroformylation of 1-hexene in supercritical carbon dioxide*, Catalysis Communications 4 309-314 (2003)), zeolites (see Mukhopadhyay et al., *Encapsulated HRh(CO)—(PPh₃)₃ in microporous and mesoporous supports: novel heterogeneous catalysts for hydroformylation*, Chemical Materials 15 1766-1777 (2003)), nanotubes (see Yoon et al., *Rh-based olefin hydroformylation catalysts and the change of their catalytic activity depending on the size of immobilizing supporters*, Inorganica Chimica Acta. 345 228-234 (2003)), supported aqueous phase catalysis ("SAPC") (see Dessoudeix et al., *Apatitic tricalcium phosphate as novel smart solids for supported aqueous phase catalysis (SAPC)*, Advanced Synthetic Catalysis 344 406-412 (2002)), and polymers (see Lu et al., *Hydroformylation reactions with recyclable rhodium-complexed dendrimers on a resin*, Journal of American Chemical Society 125 13126-13131 (2003) and Lopez et al., *Evaluation of polymer-supported rhodium catalysts in 1-octene hydroformylation in supercritical carbon dioxide*, Industrial & Engineering Chemistry Research 42 3893-3899 (2003)). However, such approaches approach still suffers from several drawbacks as follows that prevent it from being commercially viable: (a) metal leaching from the support; (b) reduced activity and selectivity compared to the homogeneous counterpart; (c) nonuniform structures of the resulting heterogeneous catalysts; (d) mass transfer limitations due to hindered diffusion; (e) low activity; and/or (f) high operating pressures and/or temperatures.

Previously, several research groups have developed polystyrene supports that facilitate the recycle of rhodium catalysts. Uozumi et al., *VII-B-1 Amphiphilic Resin-Supported Rhodium-Phosphine Catalysts for C—C Bond Forming Reactions in Water*, Synth. Catal. 344 274 (2002); Otomaru et al., *Preparation of an Amphiphilic Resin-Supported BINAP Ligand and Its Use for Rhodium-Catalyzed Asymmetric 1,4-Addition of Phenylboronic Acid in Water*, Org. Lett. 6 3357 (2004); Miao et al., *Ionic Liquid-Assisted Immobilization of Rh on Attapulgite and Its Application in Cyclohexene Hydrogenation*, J. Phys. Chem. C 111, 2185-2190 (2007); Grubbs et al., *Catalytic reduction of olefins with a polymer-supported rhodium(I)catalyst*, J. Am. Chem. Soc. 93 3062-3063 (1971); Nozaki et al., *Asymmetric Hydroformylation of Olefins in a Highly Cross-Linked Polymer Matrix*, J. Am. Chem. Soc. 120 4051-4052 (1998); Nozaki et al., Asymmetric Hydroformylation of Olefins in Highly Crosslinked Polymer Matrixes, Bull. Chem. Soc. Jpn. 72 1911-1918 (1999); Shibahara et al., *Solvent-Free Asymmetric Olefin Hydroformylation Catalyzed by Highly Cross-Linked Polystyrene-Supported (R,S)-BINA-PHOS-Rh(I) Complex*, J. Am. Chem. Soc. 125 8555-8560 (2003). However, the typical polymer supports suffer from serious limitations like insolubility, gel formation, tedious procedures to swell the polymer, and limited loading of the phosphorus ligand in the polymer backbone (e.g., 0.17 mmol/g). Many of these issues relate to the fact that polymers that are purchased commercially, or are prepared by conventional radical polymerization of styrene, have high molecular weight and/or broad molecular weight distribution. Thus, they have poor solubility properties. The slower kinetics of reactions catalyzed by gel-phase or solid-phase catalysts have important practical effects as well. For instance, the conjugate addition of arylboronic acids to enones suffers from competing hydrolysis of the costly boronic acids; the slower the catalyst is, the more hydrolysis occurs. Thus, when a heterogeneous polystyrene-supported catalyst is used for the conjugate addition, a 4-5-fold excess of boronic acid is required.

The use of $CO_2$-expanded liquids ("CXLs") as reaction media has received increased attention by the present inventors. CXLs are a continuum of compressible media generated when various amounts of dense phase carbon dioxide are added to an organic solvent. CXLs offer both reaction and environmental benefits. Near-critical carbon dioxide possesses highly tunable transport properties ranging from gas-like diffusivities to liquid-like viscosities. See Subramaniam et al., *Reaction in supercritical fluids—a review*, Industrial & Engineering Chemistry Process Design and Development 25 1-12 (1986). The presence of dense $CO_2$ imparts similar tunability to CXLs as well. The solubilities of many gaseous reagents (i.e., $O_2$, $H_2$) in CXLs are enhanced several-fold relative to the neat liquid phase (i.e., those without any CXLs). See Hert et al., *Enhancement of oxygen and methane solubility in 1-hexyl-3-methylimidazolium bis(tryluoromethylsul-fonyl)imide using carbon dioxide*, Chemical Communications 2603-2605 (2005); Wei et al., *Autoxidation of 2,6-di-tertbutyl-phenol with cobalt Schiff base catalysts by oxygen in $CO_2$-expanded liquids*, Green Chemistry 6 387-393 (2004); Solinas et al., *Enantioselective hydrogenation of imines in ionic liquid/carbon dioxide media*, Journal of American Chemical Society 126 16142-16147 (2004); Bezanehtak et al., *Vapor-liquid equilibrium for the carbon dioxide+hydrogen+methanol ternary system*, Journal of Chemical Engineering Data 49 430-434 (2004); Xie et al., *Bubble and dew point measurements of the ternary system carbon dioxide+methanol+hydrogen at 313.2 K*, Journal of Chemical Engineering Data 50 780-783 (2005). Although most transition metal complexes are only sparingly soluble in supercritical $CO_2$ ($scCO_2$), the presence of an appropriate amount of the organic liquid in CXLs ensures adequate solubilities of transition metal complexes in a CXL phase for performing homogeneous catalysis. Further, such solubilities are realized at pressures an order of magnitude lower than those required in $scCO_2$ medium for solubilizing Rh catalyst complexes with fluorinated ligands. See Palo et al., *Effect of ligand modification on rhodium-catalyzed homogeneous hydroformylation in supercritical carbon dioxide*, Organometallics 19 81-86 (2000).

Recently, the present inventors reported the homogeneous catalytic hydroformylation of 1-octene in $CO_2$-expanded acetone with an unmodified rhodium catalyst. See Jin et al. *Homogeneous catalytic hydroformylation of 1-octene in $CO_2$-expanded solvent media*, Chemical Engineering Science 59 4887-4893 (2004). At 30 and 60° C., the turnover frequencies ("TOFs") in $CO_2$-expanded acetone were up to four-fold greater than those obtained in either neat acetone (a polar solvent) or compressed $CO_2$. The enhanced rates in CXLs were realized at significant solvent replacement (up to 80% by volume) and at mild operating pressures (less than 12 MPa). Although the hydroformylation rates were enhanced, the regioselectivity towards linear and branched aldehydes (n/i ratio) remained unaffected by the change in either the acetone/$CO_2$ ratio or the temperature. In Subramaniam et al., U.S. Pat. No. 7,365,234, which is incorporated by reference, an improved hydroformylation process was described. Altering the amount of the compressed gas in the liquid phase alters the chemoselectivity of the products. In addition, varying the content of the compressed gas in the liquid alters the regioselectivity of the products. The addition of the increasing amounts of the compressed gas surprisingly improves the ratio of linear to branched aldehydes during the hydroformylation process, and vice-versa.

In the present invention, soluble polymer-supported rhodium catalysts that have a narrow molecular weight distribution were prepared. These compounds can be readily recycled by precipitation and filtration. In addition to molecular weight control, it was important to design a polymer support that could bind Rh in a multidentate fashion. Such binding was expected to better site-isolate the rhodium catalysts as well as prevent leaching of rhodium from the polymer. Moreover, it was demonstrated that such catalysts can be employed using CXLs.

BRIEF SUMMARY OF THE INVENTION

The present invention is directed to novel catalyst compositions and their methods of use. The catalyst composition comprises polymer that is functionalized with a multidentate ligand for binding a transition metal containing compound. The functionalized polymer forms a transition metal complex with the transition metal. In one aspect, the functionalized polymer has a number average molecular weight of about 5,000 to 30,000 g/mol and a polydispersity index of about 1.0 to 2.0. In another aspect, the functionalized polymer has a number average molecular weight of about 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000 g/mol, or some range therebetween. For example, the functionalized polymer may have a number average molecular weight selected from a range consisting of about 6,000 to 25,000 g/mol, 7,000 to 20,000 g/mol, 8,000 to 15,000 g/mol, and 9,000 to 12,000 g/mol. In still another aspect, the polydispersity index is about 1.0, 1.1, 1.2, 1.3, 1.4, 1.5, 1.6, 1.7, 1.8, 1.9, 2.0, or some range therebetween. The preferred catalyst composition comprises polystyrene-co-6,6'-(3,3'-di-tert-butyl-5,5'-divinylbiphenyl-2,2' diyl)bis(oxy)didibenzo[1,3,2]dioxaphosphepine.

In another aspect, the functionalized polymer is selected from the group consisting of polystyrene, polyethylene glycol, poly(vinylpyrrolidine), poly(ethylene oxide), poly(vinyl chloride), polyethylenimine, polyacrylonitrile, poly(ethyleniminodiacetic acid), polyphazene, polysiloxanes, polyacrylamide, or a dendrimeric polymer, including block or copolymers thereof. The functional groups may be attached to the polymer chain by copolymerization with one or more monomers (e.g. compound (5) in Example 1 and styrene as described herein). Alternatively, the functionalized polymer may be prepared by functionalizing the already formed polymer, for example as shown in Bergbreiter, *Using Soluble Polymers to Recover Catalysts and Ligands*, Chem. Rev. 102 (10), 3345-3384 (2002), which is incorporated by reference. The functionalized polymer may be cross-linked or uncrosslinked. In one aspect, the polymer is cross-linked and has a crosslinker ratio ranging from 8 to 12 in moles of monomer to moles of crosslinking monomer. Exemplary classes of polymer backbones are disclosed in Bergbreiter, *Using Soluble Polymers to Recover Catalysts and Ligands*, Chem. Rev. 102(10) 3345-3384 (2002), which is incorporated by reference.

In one aspect, the functionalized polymer, such as polystyrene, preferably has at least one moiety selected from the group consisting of amino, epoxy, carboxylic acid, carboxylic ester, ortho ester, anhydride, carbon-carbon double bond, phosphine, phosphite, and pyridyl. In another aspect, functionalized polymer is selected from the group consisting of a copolymer of polystyrene or polyethylene glycol, and the ligand comprises a phosphine, phosphinane, phosphinine, phosphinite, phosphite, or phosphonite moiety. An exemplary functionalized polymer includes a phosphite-based bidentate ligand. The bis(phosphate) functionalized polymer ligand is able to sequester the transition metal (rhodium) with two phosphites.

In another aspect, the catalyst composition has a transition metal complex which is covalently bound or chelated to said polystyrene at a ratio of about 1:10 to 1:20 mol:mol in terms of mole metal to mole of styrene monomer.

In another aspect, transition metal of said transition metal complex is selected from the group consisting of rhodium, cobalt, iridium, ruthenium, nickel, palladium, and platinum.

In still another aspect, the present invention is directed to a reaction mixture comprising a reactant, a substrate, and the catalyst composition as described herein. The reaction mixture is preferably a hydrogenation reaction mixture, a hydroformylation reaction mixture, an oxidation reaction mixture, or a carbonylation reaction mixture, or a combination thereof.

At least a portion of the reaction mixture is preferably in a liquid phase. Preferably the substrate and catalyst are in the liquid phase. The reactant may also be in the liquid phase (for example, oxidation of an oxidizable substrate using hydrogen peroxide). The substrate in the reaction mixture may include a ketone, aldehyde, enone, enal, olefin, alkyne, alcohol, oxidizable substrate, or mixtures thereof. The reactant may include a reactant gas selected from the group consisting of $CO$, $O_2$, $H_2$, or a $H_2/Co$ syngas.

In another aspect, a compressed gas is added to the reaction mixture. The compressed gas is preferably an inert gas, such as one selected from the group consisting of nitrogen, carbon dioxide, xenon, $SF_6$, argon, or helium. It will be appreciated that the reactant may comprise a reactant gas which is also the compressed gas.

In still another aspect, a compressed gas is added to the reaction mixture to volumetrically expand the reaction mixture. The addition of the compressed gas also reduces the viscosity of the liquid phase of the reaction mixture. Thus, for example, the invention provides for an improved hydroformylation process comprising reacting an olefin with CO and $H_2$ in the presence of the inventive hydroformylation catalyst composition in a liquid that has been volumetrically expanded with a compressed gas, such as supercritical or subcritical carbon dioxide.

The compressed expanding gas is generally selected from the group consisting of carbon dioxide, $N_2O$, xenon, and $SF_6$, although for reasons of cost and ease of use, pressurized subcritical or supercritical carbon dioxide is usually the gas of choice. The expanding gas is present in the reaction mixture at a level below that which will cause the catalyst to precipitate; that is, the catalyst is usually the least soluble component of the reaction mixture, and for good results, it should remain uniformly solubilized in the reaction mixture. Therefore, the expanding gas is introduced at levels which will maintain uniform solubility of the inventive polymer-based catalyst composition with the molecular weight and narrow PDI as discussed herein. These levels of course vary depending upon the components of the reaction mixture, and especially the catalyst. It is therefore usually necessary to preliminarily determine the extent of expanding gas supplementation which can be accommodated with each individual reaction mixture. See Subramaniam, U.S. Pat. Nos. 6,740,785 and 6,740,785 titled "Catalytic oxidation of organic substrates by transition metal complexes in organic solvent media expanded by supercritical or subcritical carbon dioxide," and see Subramaniam, U.S. Pat. No. 7,365,234 titled "Tuning product selectivity in catalytic hydroformylation reactions with carbon dioxide expanded liquids," all of which are incorporated by reference. The compressed gas typically has a volume fraction in the liquid phase between 10% and 90%. As discussed above, it will be appreciated that the reactant may comprise a reactant gas which is also the compressed gas used to volumetrically expand the liquid phase of the reaction mixture.

In another aspect, the catalyst composition comprising the polymer functionalized with a multidentate ligand of the present invention is recyclable. Thus, the present invention is also directed to a process for the separation of the catalyst composition from the reaction mixture. The process steps include forming a reaction mixture comprising a reactant, a substrate, an optional solvent, and the catalyst as described herein. The substrate and the catalyst composition are in a liquid phase. The liquid phase is then filtered through a filter to form a retentate composition and a permeate composition. The reaction and filtration steps may be performed either batchwise or continuously. Total losses of the transition metal are preferably less than 10%, still more preferably less than 5%, and are most preferably less than 2%.

Thus, in one aspect, the present invention uses nanofiltration by (a) specifically designing and synthesizing bulky polymer-supported catalyst complexes of transition metals (such as Rh) such that the bulky complexes are substantially retained in the retentate composition and that the leakage of Rh and other metals along with the solvent that passes through the nanofiltration membrane into the permeate composition is lowered to tens of parts per billion (ppb); (b) using compressed gas-expanded liquids, such as CXLs, to lower the viscosity (compared to conventional non-expanded liquids) of the liquid phase being filtered and thereby improving the filtration rates; and (c) performing reactions continuously using the compressed gas-expanded liquids (e.g. CXLs) in the nanofiltration device/reactor to not only exploit the advantages of process intensification and improved selectivity afforded by CXLs but also simultaneously separate the products by the nanofiltration membrane while substantially retaining the catalyst composition in the retentate composition.

As an example, the present invention is directed to a catalyst composition comprising a soluble polymer-supported bidentate phosphite ligands with a narrow molecular weight distribution and PDI which binds to Rh-containing compounds. As a result, the precipitation of the heavier molecular weight fraction of the functionalized polymer in CXLs and the leakage of the lighter molecular weight fraction of the functionalized polymer (along with the bound Rh) through the membrane are simultaneously avoided. The precipitation and leakage cause losses of catalyst activity and metal, both of which are detrimental to process economics. Further, the use of a compressed gas such as $CO_2$ not only provides the pressure for nanofiltration but also lowers the viscosity of the solution by partly dissolving in the solution without causing precipitation of the complex.

The hydroformylation and other reactions using the catalyst composition of the present invention preferably occur at a pressure range selected from the group consisting of 0.2 to 30 MPa, 0.3 to 20 MPa, 0.5 to 10 MPa, and 1 to 5 MPa. The reactions using the catalyst composition of the present invention preferably take place at a temperature range selected from the group consisting of 10 to 200° C., 15 to 150° C., 20 to 100° C., and 25-80° C. The pressure and/or temperature may be constant or may vary through the reaction.

In still another aspect, the catalyst compositions of the present invention are particularly well adapted for use in hydroformylation reactions in which the inventive polymer-supported catalyst composition is recycled. Thus, the present invention is directed to a hydroformylation process comprising forming a reaction mixture comprising CO and $H_2$ as reactants, and in which the catalyst composition comprising the functionalized polymer is complexed with a transition metal and a olefin substrate are in the liquid phase. The liquid phase has preferably been volumetrically expanded with a compressed gas, such as compressed carbon dioxide, by adding a adding a compressed gas into the reaction mixture. The liquid phase is then passed through a filter to form a retentate composition and a permeate composition such that the retentate composition retains the catalyst composition and is recycled. The preferred hydroformylation catalyst composition comprises a rhodium containing compound and a phosphorous-containing ligand in the polymer, such as a bis(phosphite) polystyrene. An organic solvent, such as acetone, toluene, tetrahydrofuran, or dichloromethane, may be added to the reaction mixture in the liquid phase. The process is preferably maintained at a temperature between 30° C. and 90° C. and a pressure less than 12 MPa. The reaction and filtration steps may be performed either batchwise or continuously.

As discussed herein, the catalyst compositions are recyclable using nanofiltration technologies. It is anticipated that the permeate composition has a concentration of the transition metal less than 100 ppb, preferably less than 50 ppb, and even less than 30 ppb. For example, for the exemplary catalyst composition described herein, rhodium retentate concentrations were about 250 ppm, while the rhodium permeate concentrations were under 30 ppb.

In still another aspect, the catalyst compositions of the present invention may used in oxidation reactions in which the metal catalyst composition is recycled. The compressed gas may comprise one selected from the oxygen, air, or a combination thereof. Hydrogen peroxide may also be used as an oxidant by providing the hydrogen peroxide in the liquid phase, along with the substrate. The reaction and filtration steps may be performed either batchwise or continuously.

In still another aspect, the catalyst compositions of the present invention are used in hydrogenation reactions in which the metal catalyst is recycled. The compressed gas comprises $H_2$. The reaction and filtration steps may be performed either batchwise or continuously.

In still another aspect, the catalyst compositions of the present invention are used in a carbonylation reaction in which the metal catalyst is recycled. The compressed gas compressed gas comprises CO. The reaction and filtration steps may be performed either batchwise or continuously.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1A:
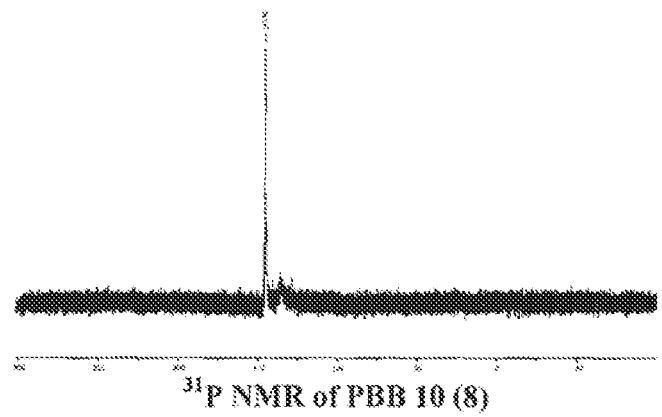
FIG. 1A shows the $^{31}P$ NMR for compound PPB 10 (8)

As used herein, the term "carbon dioxide expanded liquids" or "CXLs" refer to a continuum of compressible media generated when a dense phase carbon dioxide is added to an organic liquid media. Pressurized subcritical or supercritical carbon dioxide is usually the gas of choice.

As used herein, the term "higher olefins" refers to olefins having more than five carbons in the chain.

As used herein, the term "internal" olefins are accordingly olefins whose double bond is, unlike alpha-olefins, not terminal but located in the interior of the olefin molecule.

As used herein, the term "turnover frequency" or "TOF" refers to a moles of substrate (e.g., 1-octene) converted to all products per mole of catalyst per hour during fixed-time batch runs.

As used herein, the term "chemoselectivity" or "$S_a$" refers to the moles of aldehydes or the octene isomers formed relative to the moles of substrate (e.g., octene) converted during the hydroformylation process.

As used herein, the term "regioselectivity" or "n/i" refers to the ratio of linear to branched aldehydes in the product.

As used herein, the term "transition metal complex" means a discrete molecule that contains a transition metal ion and a ligand attached to polymer backbone. In one aspect, the transition metal complexes are coordination compounds. In another aspect, the metal complexes are "organometallic complexes," meaning that the complex is between the transition metal ion and a carbon on a ligand comprising a carbon-containing compound. Suitable transition metals for forming the metal complex starting materials of the present invention include the transition metals, e.g., Co, Cr, Fe, V, Mg, Ni, Ru, Zn, Al, Sc, Zr, Ti, Sn, La, Os, Yb, and Ce. Preferred transition metal ions are selected from the group consisting of rhodium, cobalt, iridium, ruthenium, nickel, palladium, and platinum.

As use herein the term "polydispersity" or "polydispersity index" refers to the relationship between the weight average molecular weight of the polymer and the number average molecular weight of the polymer. Specifically, the polydispersity index is the ratio between weight average molecular weight and number average molecular weight.

The present invention is directed to novel catalyst compositions and their methods of use. The catalyst compositions comprise a polymer that is functionalized with a multidentate ligand for binding a transition metal containing compound. The functionalized polymer forms a transition metal complex with the transition metal. The functionalized polymer has a number average molecular weight of about 5,000 to 30,000 g/mol and a polydispersity index of about 1.0 to 2.0. In another aspect, the functionalized polymer has a number average molecular weight of about 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000 g/mol, or some range therebetween. For example, the functionalized polymer may have a number average molecular weight selected from a range consisting of about 6,000 to 25,000 g/mol, 7,000 to 20,000 g/mol, 8,000 to 15,000 g/mol, and 9,000 to 12,000 g/mol. The polydispersity index is about 1.0, 1.1, 1.2, 1.3, 1.4, 1.5, 1.6, 1.7, 1.8, 1.9, 2.0, or some range therebetween.

The functionalized polymer is selected from the group consisting of polystyrene, polyethylene glycol, poly(vinylpyrrolidine), poly(ethylene oxide), poly(vinyl chloride), polyethylenimine, polyacrylonitrile, poly(ethyleniminodiacetic acid), polyphazene, polysiloxanes, polyacrylamide, or a dendrimeric polymer, including block or copolymers thereof. The functional groups may be attached to the polymer chain by copolymerization with one or more monomers (e.g. compound (5) in Example 1 and styrene as described herein). Alternatively, the functionalized polymer may be prepared by functionalizing the already formed polymer, for example as shown in Bergbreiter, *Using Soluble Polymers to Recover Catalysts and Ligands*, Chem. Rev. 102(10), 3345-3384 (2002), which is incorporated by reference. The functionalized polymer may be cross-linked or uncrosslinked. In one aspect, the polymer is cross-linked and has a crosslinker ratio ranging from 8 to 12 in moles of monomer to moles of crosslinking monomer. Exemplary classes of polymer backbones are disclosed in Bergbreiter, *Using Soluble Polymers to Recover Catalysts and Ligands*, Chem. Rev. 102(10) 3345-3384 (2002), which is incorporated by reference.

The functionalized polymer, such as polystyrene, preferably has at least one moiety selected from the group consisting of amino, epoxy, carboxylic acid, carboxylic ester, ortho ester, anhydride, carbon-carbon double bond, phosphine, phosphite, and pyridyl. In another aspect, functionalized polymer is selected from the group consisting of a copolymer of polystyrene or polyethylene glycol, and the ligand comprises a phosphine, phosphinane, phosphinine, phosphinite, phosphite, or phosphonite moiety, such as those disclosed herein. An exemplary functionalized polymer includes a phosphite-based bidentate ligand. The bis(phosphate) functionalized polymer ligand is able to sequester the transition metal (rhodium) with two phosphites.

The present invention is directed to a reaction mixture comprising a reactant, a substrate, and the catalyst composition as described herein. The reaction mixture is preferably a hydrogenation reaction mixture, a hydroformylation reaction mixture, an oxidation reaction mixture, or a carbonylation reaction mixture, or a combination thereof.

Hydroformylation Reaction Mixtures

The hydroformylation is carried out in a homogeneous reaction system. The term "homogeneous reaction system" generally refers to a homogeneous solution comprised of gas-expanded solvent (e.g. CXLs), the catalyst composition as described herein, a syngas, and olefinically unsaturated compound, and the reaction product.

The amount of rhodium compound (or other transition metal compound) in the catalyst composition is not specially limited, but is optionally selected so that favorable results can be obtained with respect to catalyst activity and economy. In general, the concentration of rhodium in the reaction medium is between 10 and 10,000 ppm and more preferably between 50-500 ppm, calculated as the free metal.

The volume ratio of carbon monoxide to hydrogen in the synthesis gas is generally in the range from 10 to 1 and 1 to 10, preferably between 6 to 1 to 1 to 6, and most preferably 2:1 to 1:2, in particular 1:1. The synthesis gas is advantageously used in excess, for example in an amount up to three times the stoichiometric amount.

The olefin substrates in the present invention may be any organic compound having at least one ethylenically unsaturated functional group (i.e., a carbon-carbon double bond) and may be, for example, an aromatic, aliphatic, mixed aromatic-aliphatic (e.g., aralkyl), cyclic, branched or straight chain olefin. Preferred olefins are $C_2$ to $C_{20}$ olefins, and most preferred are "higher olefins" which refers to compounds containing more than 5 carbon atoms. More than one carbon-carbon double bond may be present in the olefin, and thus, dienes, trienes, and other polyunsaturated substrates thus may be used. The olefin may optionally contain substituents other than hydrocarbon substituents such as halide, carboxylic acid, ether, hydroxy, thiol, nitro, cyano, ketone, ester, anhydride, amino, and the like.

Exemplary olefins suitable in the process of the present invention include ethylene, propylene, butenes, butadiene, pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene decene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters), and alkenyl aromatic compounds such as styrene, alpha-methyl styrene, beta-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

In an exemplary aspect, the olefin is a fatty compound, for example, mono- and polyunsaturated free fatty acids, fatty esters, triglyceride oils, or other fatty-derived materials. Suitable olefins are described in Frankel, U.S. Pat. No. 4,083,816, which is incorporated by reference.

Of these, linear higher olefins are most preferred. The olefin is preferably present in about 0.1 to 99.99 mol % of the reaction mixture. It will be appreciated to those skilled in the art that the olefin concentration (i.e., availability) in the liquid phase, where the reaction occurs, is most important, and for low boiling light olefins this is dictated by the operating pressure and temperature.

The hydroformylation catalyst composition of the present invention comprises any transition metal capable of carrying out catalytic transformations. Any of the transition metals may be considered in this regard. The preferred metals are those comprising Group VIII (Groups 8-10) of the Periodic Table. The preferred metals for hydroformylation are rhodium, cobalt, iridium, ruthenium, palladium, and platinum. The Group VIII metal is preferably rhodium.

Group VIII catalysts suitable for hydroformylation, can be prepared or generated according to techniques well known in the art.

The ligands to be incorporated into the polymer can be monodentate or polydentate, and in the case of chiral ligands, either the racemate or one enantiomer or diastereomer can be used. Preferred ligands are ligands which contain nitrogen, phosphorus, arsenic, or antimony as donor atoms; particular preference is given to phosphorus-containing ligands, such as phosphines, phosphine oxides, phosphinanes, phosphinines, phosphinites, phosphites, and phosphonites.

Examples of phosphines are triphenylphosphine, tris(p-tolyl)phosphine, tris(m-tolyl)phosphine, tris(o-tolyl)phosphine, tris(p-methoxyphenyl)phosphine, tris(p-fluorophenyl)phosphine, tris(p-chlorophenyl)phosphine, tris(p-dimethylaminophenyl)phosphine, ethyldiphenylphosphine, propyldiphenylphosphine, t-butyldiphenylphosphine, n-butyldiphenylphosphine, n-hexyldiphenylphosphine, c-hexyldiphenylphosphine, dicyclohexylphenylphosphine, tricyclohexylphosphine, tricyclopentylphosphine, triethylphosphine, tri(1-naphthyl)phosphine, tri-2-furylphosphine, tribenzylphosphine, benzyldiphenylphosphine, tri-n-butylphosphine, tri-i-butylphosphine, tri-t-butylphosphine, bis(2-methoxyphenyl)phenylphosphine, neomenthyldiphenylphosphine, 1,2-bis(dicyclohexylphosphino)ethane, bis(dicyclohexylphosphino)methane, 1,2-bis(diethylphosphino)ethane, 1,2-bis(2,5-diethylphospholano)benzene [Et-DUPHOS], 1,2-bis(2,5-diethylphospholano)ethane [Et-BPE], 1,2-bis(dimethylphosphino)ethane, bis(dimethylphosphino)methane, 1,2-bis(2,5-dimethylphospholano)benzene [Me-DUPHOS], 1,2-bis(2,5-dimethylphospholano)ethane [Me-BPE], 1,2-bis(diphenylphosphino)benzene, 2,3-bis(diphenylphosphino)bicyclo[2.2.1]hept-5-ene [NORPHOS], 2,2'-bis(diphenylphosphino)-1,1'-binaphthyl [BINAP], 2,2'-bis(diphenylphosphino)-1,1'-biphenyl [BISBI], 2,3-bis(diphenylphosphino)butane, 1,4-bis(diphenylphosphino)butane, 1,2-bis(diphenylphosphino)ethane, bis(2-diphenylphosphinoethyl)phenylphosphine, 1,1'-bis(diphenylphosphino)ferrocene, bis(diphenylphosphino)methane, 1,2-bis(diphenylphosphino)propane, 2,2'-bis(di-p-tolylphosphino)-1,1'-binaphthyl, O-isopropylidene-2,3-dihydroxy-1,4-bis(diphenylphosphino)butane [DIOP], 2-(diphenylphosphino)-2'-methoxy-1,1'-binaphthyl, 1-(2-diphenylphosphino-1-naphthyl)isoquinoline, 1,1,1-tris(diphenylphosphino)ethane, and/or tris(hydroxypropyl)phosphine.

Examples of phosphinanes include 2,6-bis(2,4-dimethylphenyl)-1-octyl-4-phenylphosphinane, 1-octyl-2,4,6-triphenylphosphinane and further ligands described in WO 02/00669.

Examples of phosphinines include 2,6-dimethyl-4-phenylphosphinine, 2,6-bis(2,4-dimethylphenyl)-4-phenylphosphinine and also further ligands described in WO 00/55164.

Examples of phosphites are trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl)phosphite, triphenyl phosphite, tris(2,4-di-t-butylphenyl)phosphite, tris(2-t-butyl-4-methoxyphenyl) phosphite, tris(2-t-butyl-4-methylphenyl)phosphite, tris(p-cresyl)phosphite. Further examples are sterically hindered phosphite ligands as are described, inter alia, in EP 155 508; U.S. Pat. No. 4,668,651; U.S. Pat. No. 4,748,261; U.S. Pat. No. 4,769,498; U.S. Pat. No. 4,774,361; U.S. Pat. No. 4,835,299; U.S. Pat. No. 4,885,401; U.S. Pat. No. 5,059,710; U.S.

Pat. No. 5,113,022; U.S. Pat. No. 5,179,055; U.S. Pat. No. 5,260,491; U.S. Pat. No. 5,264,616; U.S. Pat. No. 5,288,918; U.S. Pat. No. 5,360,938; EP 472 071; EP 518 241; and WO 97/20795. Triphenyl phosphites which are substituted by 1 or 2 isopropyl and/or tert-butyl groups on the phenyl rings, preferably in the ortho position relative to the phosphite ester group, are preferably used. Bisphosphite ligands which are described, inter alia, in EP 1 099 677; EP 1 099 678; WO 02.00670; JP 10279587; EP 472017; WO 01/21627; WO 97/40001; WO 97/40002; U.S. Pat. No. 4,769,498; EP 213639; and EP 214622, are particularly preferably used.

Customary phosphinite ligands are described, inter alia, in U.S. Pat. No. 5,710,344; WO 95 06627; U.S. Pat. No. 5,360, 938; and JP 07082281. Examples are diphenyl(phenoxy) phosphine and its derivatives in which all or some of the hydrogen atoms are replaced by alkyl or aryl radicals or halogen atoms, diphenyl(methoxy)phosphine, diphenyl (ethoxy)phosphine, etc.

Examples of phosphonites are methyldiethoxyphosphine, phenyldimethoxyphosphine, phenyldiphenoxyphosphine, 6-phenoxy-6H-dibenz[c,e][1,2]oxaphosphorin and their derivatives in which all or some of the hydrogen atoms are replaced by alkyl or aryl radicals or halogen atoms and ligands as described in WO 98/43935; JP 09-268152; and DE 198 10 794, and in the German patent applications DE 199 54 721 and DE 199 54 510.

The structures of the exemplary catalysts investigated are summarized in Subramaniam et al., U.S. Pat. No. 7,365,234, which is incorporated by reference.

The rhodium concentration in the liquid reaction mixture is generally from 10 to 500 ppm by weight, preferably from 30 to 350 ppm by weight and particularly preferably from 50 to 300 ppm by weight.

The hydroformylation process of the present invention can advantageously be carried out in the presence of solvents. In general, the polarity of the solvent will impact the regioselectivity, with non-polar solvents generally yielding higher n/i ratios. Adding a compressed gas such as $CO_2$ to the solvent allows for the continuous tunability of the polarity of the solvent system towards a more non-polar system. As solvents, preference is given to using the aldehydes which are formed in the hydroformylation of the respective olefins and also their higher-boiling downstream reaction products, i.e., the products of aldol condensation. Solvents which are likewise suitable are the olefins themselves, aromatics such as toluene and xylenes, hydrocarbons or mixtures of hydrocarbons, which can also serve for diluting the above-mentioned aldehydes and the downstream products of the aldehydes. Further possible solvents are esters of aliphatic carboxylic acids with alkanols, for example ethyl acetate or Texano®, ethers such as tert-butyl methyl ether and tetrahydrofuran. Is also possible to use non-polar solvents, e.g., alcohols such as methanol, ethanol, n-propanol, isopropanol, n-butanol, isobutanol, ketones such as acetone, and methyl ethyl ketone etc. "Ionic liquids" can also be used as solvents. These are liquid salts, for example, N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, e.g., the tetrafluoroborates, acetates, tetrachloroaluminates, hexafluorophosphates, chlorides, and tosylates.

Other Reaction Mixture Systems

It is also anticipated that the catalyst compositions herein and the methods for retention and recycling of the catalyst compositions during either batch or continuous operation may be readily adapted to other reaction mixture systems in addition to hydroformylation systems, such as a hydrogenation reaction mixture, an oxidation reaction mixture, or a carbonylation reaction mixture, or a combination thereof. See generally, Bergbreiter, *Using Soluble Polymers to Recover Catalysts and Ligands*, Chem. Rev. 102(10), 3345-3384 (2002), which is incorporated by reference. For example, Subramaniam, U.S. Pat. Nos. 6,740,785 and 6,740,785 titled "Catalytic oxidation of organic substrates by transition metal complexes in organic solvent media expanded by supercritical or subcritical carbon dioxide," which are both incorporated by reference, disclose oxidation reaction mixtures broadly including an oxidizable substrate and an oxidation catalyst that are supplemented with a compressed gas such as carbon dioxide so as to volumetrically expand the reaction mixture, thereby facilitating and accelerating oxidation. Although the expansion gas could either be a compressible gaseous substrate or the oxidizing agent, typically a substrate or an oxidizing agent separate from the inert gas is employed. Thus, the compressed gas may be selected from the group consisting of oxygen, air, or a combination thereof as the oxidizing agent. Alternatively, the oxidizing agent (such as hydrogen peroxide) may be provided in the liquid phase. The reaction mixtures generally include an organic solvent system. The catalyst compositions of the present invention may readily substituted with the transition metal complexes described therein.

Membrane Filtration

The present invention also involved methods to recycle the polymer-supported catalysts of the present invention using membrane filtration. The filter preferably has a molecular weight cut-off range selected from the group consisting of 100 to 1000 g/mol, 150 to 600 g/mol, or 200 to 500 g/mol based on 90% rejection of the solute. Several membranes have been claimed to be capable of nanofiltration in organic solvent, known as solvent resistant nanofiltration (SRNF) membranes. Koch SelRO® membrane systems (USA) are solvent-stable, commercially available, and supplied in a wet form. Among of the most popularly examined membranes (MPF-60, MPF-44 and MPF-50), MPF-50 has been the most studied commercial SRNF membrane in many applications. STARMEM® from Membrane Extraction Technology (United Kingdom) and Solsep membranes from SolSep BV-Robust Membrane Technologies (The Netherlands) appeared in the market recently and have been successfully demonstrated in the literature for organic solvent nanofiltration. Another series of membranes, Desal-5 and Desal-5-DK from GE Osmonics (USA) are designed for aqueous applications, but are also selective in SRNF. Vandezande et al., *Solvent resistant nanofiltration: separating on a molecular level*, Chemical Society Reviews 37 (2) 365-405 (2008) summarized more membrane information.

The membrane nanofiltration setups described in the literature can be categorized into two groups according to the flow direction relative to the membrane surface: dead-end filter (perpendicular) and cross-flow filter (parallel). Commercially available dead-end filtration cells include: a solvent-resistant stirred cell from Millipore (USA), MET cell from Membrane Extraction Technology Ltd. (UK) and HP4750 stirred cell from Sterlitech Corporation (USA). However, an alternative setup GE Sepa™ CF II Med/High foulant allows for cross-flow filtration with any membrane. Cross-flow filtration set-ups are described in Nair et al., *Increased catalytic productivity for nanofiltration-coupled Heck reactions using highly stable catalyst systems*, Green Chemistry 4(4) 3 19-324 (2002); Patterson et al., *Membrane selectivity in the organic solvent nanofiltration of trialkylamine bases*, Desalination 218 (1-3) 248-256 (2008); Roengpithya et al., *Towards a continuous dynamic kinetic resolution of 1-phenylethylamine using a membrane assisted, two vessel process.*, Chemical Communications (33) 3462-3463 (2007); Peeva et al., *Effect of concentration polarisation and osmotic pressure on flux in organic solvent nanofiltration*, Journal of Membrane Science 236 (1-2), 12 1-136 (2004).

The invention will be illustrated by the following non-limiting examples.

Example 1

Synthesis of Polymer Supported Phosphite Ligands

In this example, a well-characterized polymer having comparatively low molecular weight and a narrow molecular weight distribution (about $1.2 \times 10^4$ g/mol, polydispersity index=1.3) was prepared using the scheme below. Since the functional monomer (5) proved to be equally active toward polymerization as styrene, the PDI was expected to be similar to that reported for pure polystyrene. See Dollin et al., *Additive Free Stable Free Radical Polymerization of Styrene*, J. Polym. Sci. Part A 45 5487-5493 (2007). Control of the molecular weight and distribution was achieved by adopting a living free radical polymerization technique that is mediated by the stable nitroxyl radical, TEMPO. Conducting the copolymerization of the functional monomer (5) and styrene (1:10 ratio) at 123° C. produced a functional polymer whose ligand incorporation into the polystyrene backbone was estimated at 10% from the $^1$H NMR spectrum. Interestingly, end group analysis of the vinyl region of the $^1$H NMR spectrum suggests that the polymer is not cross-linked under these conditions. In other words, a single alkene in the bis-alkene 1 undergoes polymerization. The resulting polymer was deprotected and the phosphite ligands introduced onto the polymer backbone. The result is a polymer supported Biphephos derivative that was denominated "JanaPhos" or compound PBB10. If incorporation of the phosphite into the polymer was perfect, one would expect a P-loading of 1.10 mmol/g and thus the ligand loading would be 0.55 mmol/g. Estimation of the P loading by 31P NMR spectroscopy shows that the P-loading is 0.65 mmol/g. This value was further confirmed by inductively coupled plasma optical emission spectrometry ("ICP-OES") analysis of the polymer, indicating that the polymer can support 0.32 mmol of rhodium per gram of polymer.

The synthesis of soluble polymer supported phosphite ligands is shown below in the scheme below:

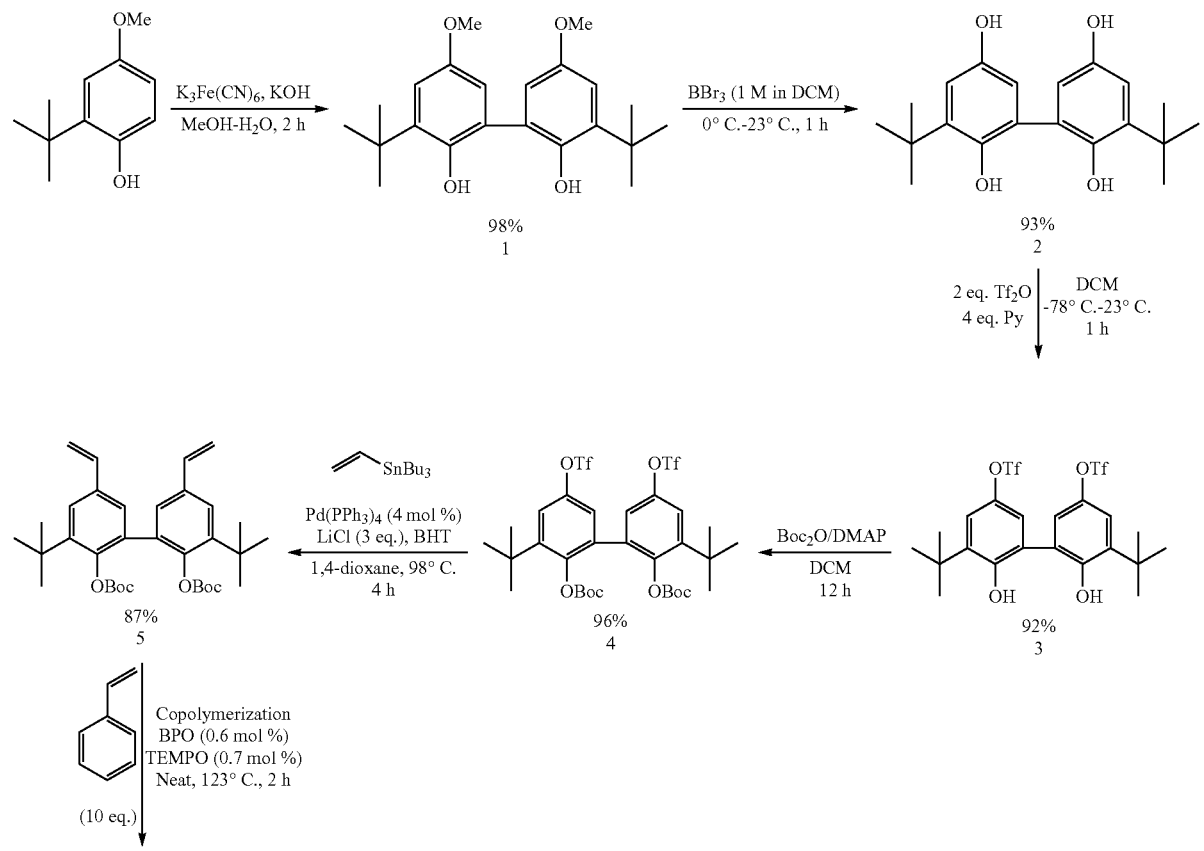

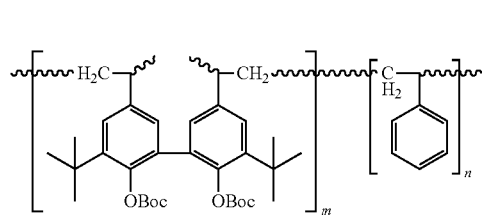

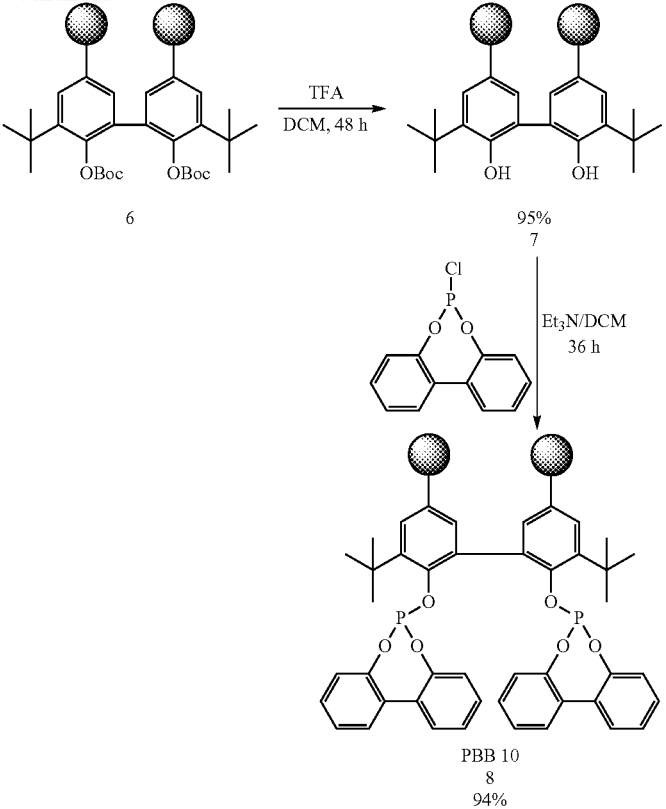

It will be appreciated that although compound PPB 10 (8) is shown with two polystyrene linkages, it is believed that the polystyrene is attached at only one of the aromatic groups shown as discussed herein.

Synthesis of 5,5'-dimethoxy-3,3'-di-tert-butylbiphenyl-2,2'-diol (1)

The compound 1 was prepared according to the reported procedure. See Vlugt et al., *Sterically demanding diphosphonite ligands—synthesis and application in nickel-catalyzed isomerization of 2-methyl-3-butenenitrile*, Adv. Synth. Catal. 346 993-1003 (2004). A solution of 3-tert-butyl-4-hydroxyanisole (10.00 g, 55.5 mmol) in methanol (300 mL) was prepared and a solution of KOH (11.07 g, 198 mmol) and $K_3Fe(CN)_6$ (18.32 g, 55.5 mmol) in water (300 mL) was added dropwise over one hour at room temperature. The mixture was stirred for two hours before the addition of 200 ml of water. The suspension was extracted with 500 mL of ethyl acetate twice. The aqueous solution was extracted with 150 ml of ether and the organic phases were combined and washed with 200 mL of saturated brine. The organic phase was dried over $Na_2SO_4$. Removal of the solvents under vacuum afforded a light brown solid. Washing with n-hexane resulted in an off-white powder; yield: 9.80 g (98%).

5,5'-Dmethoxy-3,3'-di-tert-butylbiphenyl-2,2'-diol (1)

Brownish solid, m. p. 220-222° C.; $^1$H NMR (400 MHz, $CD_2Cl_2$) δ ppm 6.99 (d, J=4.12 Hz, 2H), 6.66 (d, J=4.12 Hz, 2H), 5.15 (s, br, 2H), 3.79 (s, 6H), 1.47 (s, 18H); $^{13}$C NMR (101 MHz, $CDCl_3$) δ ppm 153.33 (2C), 145.82 (2C), 138.80 (2C), 123.55 (2C), 115.02 (2C), 111.92 (2C), 55.63 (2C), 35.03 (2C), 29.25 (6C); IR ($CH_2Cl_2$): v 3533 (br), 3001, 2985, 1596, 1414, 1392, 1215, 1159 cm$^{-1}$; Calcd. HRMS for $C_{22}H_{30}O_4$ ($M^+$) 358.2144. Found, 358.2123.

Synthesis of 3,3'-di-tert-butylbiphenyl-2,2',5,5'-tetraol (2)

To a stirring solution of 1 (3.6 g, 10 mmol) in $CH_2Cl_2$ (150 ml) borontribromide (24 ml, 24 mmol, 1 M in DCM) was added dropwise over 30 minutes at 0° C. After addition the reaction mixture was taken to room temperature and stirred for 30 minutes. It was quenched by the addition of ice water and the white precipitate was dissolved by the addition of diethyl ether. It was taken in a separatory funnel and washed with 1(N) HCl and brine, dried over anhydrous $Na_2SO_4$. Removal of the solvent under reduced pressure leaves a white chalky solid which is sufficiently pure for the next reaction. Yield (3.1 g, 93%).

3,3'-di-tert-Butylbiphenyl-2,2',5,5'-tetraol (2)

Colorless chalky solid, m. p. 224° C.; $^1$H NMR (400 MHz, DMSO-$d^6$) δ ppm 8.88 (s, 2H), 8.41 (s, 2H), 6.71 (d, J=4.00 Hz, 2H), 6.51 (d, J=4.00 Hz, 2H), 1.38 (s, 18H); $^{13}$C NMR (101 MHz, $CDCl_3$) δ ppm 151.46 (2C), 144.14 (2C), 140.81 (2C), 131.58 (2C), 115.41 (2C), 113.65 (2C), 35.10 (2C), 30.32 (6C); IR ($CH_2Cl_2$): v 3533 (br), 3001, 2985, 1596, 1414, 1392, 1215, 1159, 927, 741 cm$^{-1}$; Calcd. HRMS for $C_{20}H_{26}O_4$ (M+1), 331.1909. Found, 331.1912.

Synthesis of 5,5'-di-tert-butyl-6,6'-dihydroxybiphenyl-3,3'-diyl bis(trifluoromethanesulfonate) (3)

Compound 2 (3.30 g, 10 mmol) was dissolved in 250 ml of dry dichloromethane. The solution was cooled to −78° C. and pyridine (3.2 ml, 40 mmol) was added dropwise to it. A dilute solution of triflic anhydride (3.5 ml, 20 mmol) in dichloromethane (100 ml) was added to it over a period of one hour. After addition the reaction mixture was taken to room temperature and stirred for 30 minutes. Then the reaction mixture was partitioned between $Et_2O$, brine and 1 (N) HCl. The organic layer was washed with water, brine and dried over anhydrous $Na_2SO_4$. It was filtered and concentrated under vacuum. Purification by flash chromatography on silica gel provided the light brown gummy liquid, (5.24 g, 92% yield).

5,5'-di-tert-butyl-6,6'-dihydroxybiphenyl-3,3'-diyl bis(trifluoromethanesulfonate) (3)

Gummy liquid; $^1H$ NMR (400 MHz, $CDCl_3$) δ ppm 7.29 (d, J=4.00 Hz, 2H), 7.04 (d, J=4.0 Hz, 2H), 5.37 (s, br, 2H), 1.44 (s, 18H); $^{13}C$ NMR (101 MHz, $CDCl_3$) δ ppm 151.66 (2C), 142.88 (2C), 140.56 (2C), 122.28 (2C), 121.87 (2C), 121.24 (2C), 121.19, 120.36, 117.17, 114.17, 113.96 ($2SO_2CF_3$), 35.47 (2C), 29.19 (6C); IR ($CH_2Cl_2$): v 3554 (br), 2970, 1583, 1425, 1371, 1263, 1245, 1217, 745 $cm^{-1}$; Calcd. HRMS for $C_{22}H_{24}F_6O_8S_2$ (M+Na), 617.0714. Found, 617.0716.

Synthesis of 6,6'-bis(tert-butoxycarbonyloxy)-5,5'-di-tert-butylbiphenyl-3,3'-diyl bis(trifluoromethanesulfonate) (4)

To a stirring solution of 3 (5.94 g, 10 mmol) in $CH_2Cl_2$ (120 ml) was added di-tert-butyldicarbonate (5.5 ml, 24 mmol) and 4-dimethylaminopyridine (0.12 g, 1.0 mmol). The resulting solution was stirred overnight at 25° C. and then partitioned between $Et_2O$, brine and 1 (N) HCl. The organic layer was washed twice with aqueous $NaHCO_3$, once with brine, dried over anhydrous $Na_2SO_4$, filtered and concentrated under vacuum. Purification by flash chromatography on silica gel provided the colorless solid, which was recrystallized in hexane (7.62 g, 96% yield).

6,6'-bis(tert-Butoxycarbonyloxy)-5,5'-di-tert-butylbiphenyl-3,3'-diyl bis(trifluoromethanesulfonate) (4)

Colourless solid, m. p. 132-134° C.; $^1H$ NMR (400 MHz, $CD_2Cl_2$) δ ppm 7.39 (d, J=4.00 Hz, 2H), 7.17 (d, J=4.0 Hz, 2H), 1.45 (s, 18H), 1.23 (s, 18H); $^{13}C$ NMR (101 MHz, $CDCl_3$) δ ppm 150.12 (2C), 146.72 (2C), 146.28 (2C), 145.33 (2C), 133.61 (2C), 122.62 (2C), 120.76 (2C), 123.57, 120.39, 117.20, 114.01 ($2SO_2CF_3$), 83.49 (2C), 35.27 (2C), 29.80 (6C), 26.91 (6C); IR ($CH_2Cl_2$): v 3053, 2985, 2304, 1760, 1425, 1263, 1245, 1217, 1139, 746 $cm^{-1}$; Calcd. HRMS for $C_{32}H_{40}F_6O_{12}S_2$ (M+Na), 817.1763. Found, 817.1719.

Synthesis of tert-butyl 3,3'-di-tert-butyl-5,5'-divinylbiphenyl-2,2'-diyl dicarbonate (5)

Compound 4 (4.76 g, 6.0 mmol) was dissolved in 80 ml of dry 1,4-dioxane. Tri-n-butyl(vinyl)tin (4.2 ml, 13.2 mmol), $Pd(PPh_3)_4$ (0.28 g, 0.24 mmol), lithium chloride (1.52 g, 36 mmol) and few crystals of 2,6-di-tert-butyl-4-methylphenol was added to it. The reaction mixture was refluxed at 98° C. for four hours. After the reaction is complete (TLC) it was cooled to room temperature. After removal of dioxane, the residues were dissolved in $Et_2O$ and then 5% aqueous KF was added. The resulting solution was stirred at 25° C. for two hours. The solution was separated and followed by extraction with $Et_2O$ (3×50 ml). The organic portions were combined and washed once with brine, dried over anhydrous $Na_2SO_4$. After removal of the solvent under reduced pressure crude material was obtained which was purified by column chromatography on silica gel with ethyl acetate:hexane (10:90). Colourless solid was obtained by recrystallization in MeOH (2.8 g, 87% yield).

tert-Butyl 3,3'-di-tert-butyl-5,5'-divinylbiphenyl-2,2'-diyl dicarbonate (5)

Colorless solid, m. p. 82° C.; $^1H$ NMR (400 MHz, $CDCl_3$) δ ppm 7.40 (s, 2H), 7.29 (s, 2H), 6.71 (dd, $J_1$=16.0 Hz, $J_2$=12.0 Hz, 2H), 5.70 (d, J=20.0 Hz, 2H), 5.22 (d, J=12.0 Hz, 2H), 1.44 (s, 18H), 1.15 (s, 18H); $^{13}C$ NMR (101 MHz, $CDCl_3$) δ ppm 151.21 (2C), 146.95 (2C), 141.62 (2C), 136.51 (2C), 135.29 (2C), 133.13 (2C), 127.97 (2C), 125.01 (2C), 113.79 (2C), 82.26 (2C), 34.93 (2C), 30.58 (6C), 27.33 (6C); IR ($CH_2Cl_2$): v 3088, 2877, 1757, 1580, 1475, 1456, 1397, 1275, 1216, 766 $cm^{-1}$; Calcd. HRMS for $C_{34}H_{47}O_6$ (M+1), 551.3373. Found, 551.3355.

Synthesis of poly[styrene-co-(2,2'-di-tert-butoxycarbonyloxy-3,3'-di-tert-butyl-5,5'-divinyl-1,1'-biphenyl)] (6)

A mixture of 4 (2.201 g, 4 mmol) and styrene (4.6 ml, 40 mmol) was taken in a schenck flask. TEMPO (40 mg, 0.25 mmol) and benzoylperoxide, BPO (48 mg, 0.20 mmol) were added to it and argon was bubbled through the mixture for half an hour prior to the heating. The mixture was then heated at 123° C. for four hours. It was cooled down to room temperature and poured slowly into a beaker containing MeOH (300 ml) to give a white solid precipitation. Further purification was performed by repeating the dissolution-precipitation twice with toluene/MeOH. The final product was dried under reduced pressure to give white solid. (1.25 g, 52% yield).

Poly[styrene-co-(2,2'-di-tert-butoxycarbonyloxy-3, 3'-di-tert-butyl-5,5'-divinyl-1,1'-biphenyl)] (6)

Threaded, white solid, $^1H$ NMR (500 MHz, $CD_2Cl_2$) δ ppm 7.46 (m, br, aromatic), 7.09 (m, br, aromatic), 6.63 (m, br, aromatic), 5.63 (m, C=CH, unreacted), 5.14 (m, C=CH, unreacted), 1.90 (m, br, CH—$CH_2$ polymer backbone), 1.48 (s, tert-butyl), 1.31 (s, tert-butoxy); $^{13}C$ NMR (125 MHz, $CD_2Cl_2$) δ ppm 145.82, 144.23, 135.60, 1135.45, 134.39, 132.33, 127.07, 124.93, 81.04, 39.84, 33.96, 29.45, 26.15; IR ($CH_2Cl_2$) v 3103, 3083, 3027, 3001, 1757, 1601, 1584, 1493, 1452, 1352, 1276, 1260, 745 $cm^{-1}$.

Synthesis of polystyrene-co-(3,3'-di-tert-butyl-5,5'-divinylbiphenyl-2,2'-diol) (7)

To a solution of copolymer 5 (2.0 g) in dry $CH_2Cl_2$ (60 ml) was added TFA (2.0 ml). The mixture was stirred over 48 hours at 25° C. until IR and $^1H$ NMR showed Boc was removed completely. Upon cooling to 0° C., the saturated aqueous $NaHCO_3$ was added until the solution was neutral. The organic layer was separated from the biphasic solution and the aqueous layer was extracted with $CH_2Cl_2$ (3×50 ml). The combined organic extracts were washed twice with brine, dried over $Na_2SO_4$. The solvent was removed under reduced pressure to give pale-brown solid. Further purification was performed by repeating the dissolution-precipitation twice with toluene/MeOH. The final polymer was dried under vacuum overnight. (83% yield).

Polystyrene-co-(3,3'-di-tert-butyl-5,5'-divinylbiphenyl-2,2'-diol) (7)

Threaded, white solid, $^1$H NMR (500 MHz, CD$_2$Cl$_2$): δ ppm 7.46 (m, br, aromatic), 7.09 (m, br, aromatic), 6.63 (m; br, aromatic), 1.90 (m, br, CH—CH$_2$ polymer backbone), 1.48 (m, br, tert-butyl); $^{13}$C NMR (125 MHz, CD$_2$Cl$_2$) δ 145.01, 128.96, 128.84, 127.92, 125.7, 124.90, 43.24, 39.61, 29.64; IR (CH$_2$Cl$_2$) ν 3524, 3510, 3065, 2926, 1493, 1434, 1417, 1269 1283, 1261 cm$^{-1}$.

Synthesis of polystyrene-co-6,6'-(3,3'-di-tert-butyl-5,5'-divinylbiphenyl-2,2' diyl)bis(oxy)didibenzo[1,3,2]dioxaphosphepine (8)

To a solution of copolymer 6 in CH$_2$Cl$_2$ 15 equivalent of Et$_3$N and 10 equivalent of 2,2'-bisphenoxyphosphorous chloride was added to the reaction vessel slowly at 0° C. The reaction mixture was refluxed for 36 hours. Upon cooling to 25° C., the solution was poured into dry MeOH to give white precipitates which was further purified by repeating dissolution-precipitation process three times with CH$_2$Cl$_2$/MeOH, toluene/MeOH and THF/MeOH. The final product was dried under vacuum for overnight (86% yield).

Polystyrene-co-6,6'-(3,3'-di-tert-butyl-5,5'-divinylbiphenyl-2,2' diyl)bis(oxy)didibenzo[1,3,2]dioxaphosphepine (8) or "JanaPhos"

Threaded, white solid, $^1$H NMR (500 MHz, CD$_2$Cl$_2$): δ ppm 7.46 (m, br, aromatic), 7.09 (m, br, aromatic), 6.63 (m, br, aromatic), 1.90 (m, br, CH—CH$_2$ polymer backbone), 1.48 (m, br, tert-butyl); $^{13}$C NMR: δ (125 MHz, CD$_2$Cl$_2$) 145.01, 128.96, 128.84, 127.92, 125.7, 124.90, 43.24, 39.61, 34.17, 29.92, 28.63; $^{31}$P NMR: δ ppm 145.4; IR ν (CH$_2$Cl$_2$) 3027, 2994, 2925, 2851, 1493, 1477, 1453, 1373, 1269, 1259, 1254, 1194, 768, 746, 723, 712, 697 cm$^{-1}$.

The phosphorous content in the polymer backbone (8) was estimated by the $^{31}$P NMR using triphenylphosphine as an internal standard. The phosphorous content is 1.06 mmol/g which has been further confirmed by ICP-OES analysis. Thus, ligand incorporation is 0.53 mmol/g of polymer.

Example 2

Synthesis of Polymer Supported Rhodium Catalyst

Figure 1B:
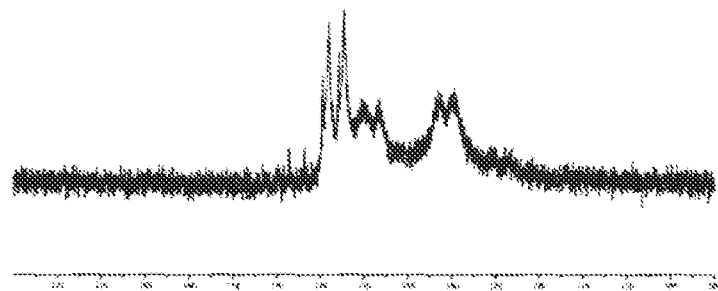
FIG. 1B shows the $^{31}P$ NMR for compound PPB 10 (8) after binding with $Rh(acac)(CO)_2$

For the following examples, the preparation of the polymer supported rhodium catalyst was performed in toluene 12 hours prior to the hydroformylation reaction. Polymer was dissolved in dry toluene (maximum solubility 60 g/l) in an inert atmosphere and Rh(acac)(CO)$_2$ (Rh/P=1/3) was added to it and stirred for overnight. The solution turns into yellowish color. The binding of the Rh with the ligand was confirmed by the $^{31}$P NMR. The change in NMR is shown in FIG. 1A and FIG. 1B.

Example 3

Hydroarylation Using Polymer-Supported Rhodium Catalyst

This example concerns the use of the catalyst compositions made according to Example 2 in the catalytic hydroarylations of enones. The typical experimental procedure is straightforward and simple to operate. A mixture of enone (1 mmol) and arylboronic acid (1.3 eq.) were placed in a round bottom flask and a toluene solution (3 mL) containing Rh(acac)(CO)$_2$ and JanaPhos as prepared in Example 2 was added to it under an inert atmosphere. Finally, a solution of methanol and water (1:1, 0.5 mL) was added to it via syringe and the resulting reaction mixture was heated at 50° C. It will be appreciated that reaction improvements have led to phosphorus loadings of 1.06 mmol/g in Example 1; however the experiments reported in this example utilized polymer with lower (0.65 mmol/g) phosphorus loading.

As can be seen from Table 1, enals, aliphatic enones, chalcones, and cyclic enones all give high yields of hydroarylation products using the catalyst. Importantly, these high yields are obtained when using just 1.3 equivalents of boronic acid partners; prior reactions using polymer-supported rhodium catalysts require 4-5 fold excess of boronic acids. In fact, the recyclable catalyst performs as well as, or better than, typical small-molecule catalysts which typically utilize 1.3-10 equivalents of boronic acid.

TABLE 1

Conjugation Addition of Phenylboronic Acid

| entry | enone | product | yield (%) |
|---|---|---|---|
| 1 | OHC-CH=CH$_2$ | OHC-CH$_2$-CH$_2$-PH | 82 |
| 2 | CH$_3$-CO-CH=CH$_2$ | CH$_3$-CO-CH$_2$-CH$_2$-PH | 86 |
| 3 | MeO-C$_6$H$_4$-CO-CH=CH-PH | MeO-C$_6$H$_4$-CO-CH$_2$-CH(Ph)-PH | 84 |

TABLE 1-continued

Conjugation Addition of Phenylboronic Acid

| entry | enone | product | yield (%) |
|---|---|---|---|
| 4 | cyclopent-2-enone | 3-phenylcyclopentanone | 92 |
| 5 | cyclohex-2-enone | 3-phenylcyclohexanone | 83 |
| 6 | cyclohept-2-enone | 3-phenylcycloheptanone | 86 |

3-Phenylpropanal (Entry 1, Table 1)

Colorless liquid, $^1$H NMR (400 MHz, CDCl$_3$) δ ppm 9.85 (t, J=4.00 Hz, 1H), 7.31-7.33 (m, 2H), 7.22-7.26 (m, 3H), 2.99 (t, J=8.00 Hz, 2H), 2.80-2.83 (m, 2H); $^{13}$C NMR (101 MHz, CDCl$_3$) δ ppm 201.70, 140.43, 128.70 (2C), 128.39 (2C), 126.40, 45.39, 28.21.

4-Phenylbutan-2-one (Entry 2, Table 1)

Colorless liquid, $^1$H NMR (400 MHz, CDCl$_3$) δ ppm 7.31 (d, J=8.13 Hz, 2H), 7.21-7.24 (m, 3H), 2.93 (t, J=8.00 Hz, 2H), 2.78 (t, J=8.00 Hz, 2H), 2.16 (s, 3H); $^{13}$C NMR (101 MHz, CDCl$_3$) δ ppm 208.02, 141.04, 128.54 (2C), 128.35 (2C), 126.15, 45.18, 30.11, 29.74.

1-(4-Methoxyphenyl)-3,3-diphenylpropan-1-one (Entry 3, Table 1)

Colorless solid, m. p. 113° C.; $^1$H NMR (400 MHz, CDCl$_3$) δ ppm 7.96 (d, J=8.13 Hz, 2H), 7.28-7.30 (m, 8H), 7.19-7.22 (m, 2H), 6.94 (d, J=8.13 Hz, 2H), 4.86 (t, J=8.17 Hz, 1H), 3.88 (s, 3H), 3.72 (d, J=4.13 Hz, 2H); $^{13}$C NMR (101 MHz, CDCl$_3$) δ ppm 196.63, 163.57, 144.39 (2C), 130.45 (2C), 130.25, 128.64 (4C), 127.96 (4C), 126.43 (2C), 113.82 (2C), 55.58, 46.13, 44.43.

3-Phenylcyclopentanone (entry 4, table 1)$^5$

Colorless liquid, $^1$H NMR (400 MHz, CDCl$_3$) δ ppm 7.36 (t, J=8.13 Hz, 2H), 7.25-7.27 (m, 3H), 3.38-3.47 (m, 1H), 2.66 (dd, J=8.12 Hz, 1H), 2.25-2.51 (m, 4H), 1.94-2.05 (m, 1H); $^{13}$C NMR (101 MHz, CDCl$_3$) δ ppm 218.51, 143.03, 128.68 (2C), 126.73 (2C), 45.81, 42.22, 38.89, 31.02.

3-Phenylcyclohexanone (Entry 5, Table 1)

Colorless liquid, $^1$H NMR (400 MHz, CDCl$_3$) δ ppm 7.36 (t, J=8.17 Hz, 2H), 7.24-7.28 (m, 3H), 3.01-3.05 (m, 1H), 2.40-2.65 (m, 4H), 2.07-2.17 (m, 2H), 1.78-1.90 (m, 2H); $^{13}$C NMR (101 MHz, CDCl$_3$) δ ppm 211.13, 144.39, 128.73 (2C), 126.74, 126.62 (2C), 49.00, 44.79, 41.24, 32.82, 25.60.

3-Phenylcycloheptanone (Entry 6, Table 1)

Colorless liquid, $^1$H NMR (400 MHz, CDCl$_3$) δ ppm 7.31-7.38 (m, 2H), 7.19-7.24 (m, 3H), 2.92-2.99 (m, 2H), 2.60-2.69 (m, 3H), 2.00-2.14 (m, 3H), 1.71-1.79 (m, 2H), 1.51-1.63 (m, 1H); $^{13}$C NMR (101 MHz, CDCl$_3$) δ ppm 213.65, 147.01, 128.75 (2C), 126.52 (2C), 126.45, 51.36, 44.05, 42.84, 39.31, 29.35, 24.27.

Next, the scope of boronic acids that can be utilized was briefly examined. More specifically, the general experimental procedure for the 1,4-addition of arylboronic acids to enones will be described using 2-cyclohexen-1-one and phenylboronic acid. A mixture of 2-cyclohexen-1-one (96 mg, 1 mmol) and phenylboronic acid (158 mg, 1.3 mmol) was taken in a round bottom flask. A toluene solution (3 ml) containing Rh(acac)(CO)$_2$ (5 mg, 0.02 mmol) and JanaPhos (70 mg, 0.03 mmol, Rh/P=1/3) was added to it in an inert atmosphere. A solution of methanol and water (1:1, 0.5 ml) was added to it via syringe. The reaction mixture was heated at 50° C. for 15 hours until the starting material was consumed as indicated by TLC. Then 25 ml methanol was added to it mixture and the catalyst was precipitated out as a white solid. It was filtered out by a Schlenk filter and underwent for the consecutive runs. The filtrate was evaporated under reduced pressure to obtain the crude product which was further purified by column chromatography (10% ethyl acetate in hexane) to obtain the pure product (144 mg, 83% yield).

Simple aryl and biaryl boronic acids all provided good yields of arylated products using a variety of enals and enones (Table 2). Moreover, dibenzylidene acetone undergoes selective monoarylation, generating only 5% of the double-addition product (Table 2, entry 4). Lastly, vinylboronic acids were suitable reaction partners, allowing access to gamma/delta-unsaturated ketones (Table 2, entries 7 and 8).

TABLE 2

Rh-Catalyzed 1,4-Addition of Boronic Acids

| entry | enone | boronic acid | product | yield (%) |
|---|---|---|---|---|
| 1 | ethyl vinyl ketone | 4-Me-C6H4-B(OH)2 | 1-(4-methylphenyl)-pentan-3-one | 87 |
| 2 | ethyl vinyl ketone | 4-Ph-C6H4-B(OH)2 | 1-(4-phenylphenyl)-pentan-3-one | 83 |
| 3 | crotonaldehyde | 4-Ph-C6H4-B(OH)2 | 3-(4-phenylphenyl)-butanal | 87 |
| 4 | dibenzylideneacetone | 4-Me-C6H4-B(OH)2 | 1-phenyl-5-(4-methylphenyl)-5-phenyl-pent-1-en-3-one | 77 |
| 5 | cyclohex-2-enone | 4-CF3-C6H4-B(OH)2 | 3-(4-trifluoromethylphenyl)-cyclohexanone | 87 |
| 6 | cyclohex-2-enone | 4-Ac-C6H4-B(OH)2 | 3-(4-acetylphenyl)-cyclohexanone | 75* |
| 7 | ethyl vinyl ketone | (E)-styryl-B(OH)2 | (E)-1-phenyl-hept-1-en-5-one | 77 |
| 8 | acrolein | (E)-styryl-B(OH)2 | (E)-5-phenyl-pent-4-enal | 82 |

1-p-Tolylpentan-3-one (Entry 1, Table 2)

Colorless liquid, $^1$H NMR (400 MHz, CDCl$_3$) δ ppm 7.10-7.15 (m, 4H), 2.91 (t, J=8.12 Hz, 2H), 2.75 (t, J=8.12 Hz, 2H), 2.44 (q, J=8.12 Hz, 2H), 2.36 (s, 3H), 1.09 (t, J=8.12 Hz, 3H); $^{13}$C NMR (101 MHz, CDCl$_3$) δ ppm 210.77, 138.11, 135.54, 129.18 (2C), 128.21 (2C), 44.06, 36.13, 29.47, 21.02, 7.79.

1-(Biphenyl-4-yl)pentan-3-one (Entry 2, Table 2)

Colorless solid, m. p. 62° C.; $^1$H NMR (400 MHz, CDCl$_3$) δ ppm 7.63 (d, J=8.12 Hz, 2H), 7.57 (d, J=8.12 Hz, 2H), 7.48 (t, J=8.00 Hz, 2H), 7.38-7.40 (m, 1H), 7.31 (d, J=8.00 Hz, 2H), 3.00 (t, J=8.00 Hz, 2H), 2.81 (t, J=8.00 Hz, 2H), 2.47 (q, J=8.00 Hz, 2H), 1.11 (t, J=8.00 Hz, 3H); $^{13}$C NMR (101 MHz, CDCl$_3$) δ ppm 210.60, 140.99, 140.36, 139.08, 128.81 (2C), 128.80 (2C), 127.25 (2C), 127.16, 127.03 (2C), 43.84, 36.18, 29.49, 7.84; IR (CH$_2$Cl$_2$): ν 2979, 2939, 1712, 1519, 1487, 1409, 1377, 1363, 1112, 831, 765 cm$^{-1}$. Calcd. HRMS for C$_{17}$H$_{18}$ONa (M+Na), 261.1255. Found, 261.1294.

3-(Biphenyl-4-yl)butanal (Entry 3, Table 2)

Colorless liquid, $^1$H NMR (400 MHz, CDCl$_3$) δ ppm 9.77 (t, J=4.00 Hz, 1H), 7.57-7.62 (m, 4H), 7.47 (t, J=8.00 Hz, 2H), 7.28-7.39 (m, 3H), 3.42-3.48 (m, 1H), 2.70-2.86 (m, 2H), 1.39 (d, J=4.00 Hz, 3H); $^{13}$C NMR (101 MHz, CDCl$_3$) δ ppm 201.93, 144.64, 140.92, 139.60, 128.85 (2C), 127.51 (2C), 127.30 (3C), 127.12 (2C), 51.83, 34.03, 22.28.

E)-1,5-diphenyl-5-p-tolylpent-1-en-3-one (Entry 4, Table 2

Colorless solid, m. p. 120° C.; $^1$H NMR (400 MHz, CDCl$_3$) δ ppm 7.48-7.53 (m, 3H), 7.37-7.39 (m, 3H), 7.26-7.27 (m, 4H), 7.14-7.7.16 (m, 3H), 7.08 (d, J=8.00 Hz, 2H), 6.69 (d, J=16.0 Hz, 1H), 4.69 (d, J=8.00 Hz, 1H), 3.41 (d, J=8.00 Hz, 2H), 2.28 (s, 3H); $^{13}$C NMR (101 MHz, CDCl$_3$) δ ppm 198.31, 144.38, 142.87, 141.14, 136.04, 134.56, 130.61, 129.37 (2C), 129.04 (2C), 128.65 (2C), 128.42 (2C), 127.88 (2C), 127.79 (2C), 126.45, 126.39, 47.17, 45.88, 21.09; IR (CH$_2$Cl$_2$): ν 3060, 2350, 16087, 1604, 1589, 1421, 1367, 1259, 757 cm$^{-1}$. Calcd. HRMS for C$_{24}$H$_{22}$ONa (M+Na), 349.1568. Found, 349.1581.

3-(4-(Trifluoromethyl)phenyl)cyclohexanone (Entry 5, Table 2)

Colorless liquid, $^1$H NMR (400 MHz, CDCl$_3$) δ ppm 7.58 (d, J=8.00 Hz, 2H), 7.33 (d, J=8.00 Hz, 2H), 3.05-3.08 (m, 1H), 2.38-2.62 (m, 4H), 2.14-2.19 (m, 1H), 2.07-2.11 (m, 1H), 1.72-1.89 (m, 2H); $^{13}$C NMR (101 MHz, CDCl$_3$) δ ppm 210.37, 148.29, 129.29, 127.09 (4C) 125.79, 122.89, 48.60, 44.58, 41.18, 32.59, 25.49.

3-(4-Acetylphenyl)cyclohexanone (Entry 6, Table 2)

Colorless liquid, $^1$H NMR (400 MHz, CDCl$_3$) δ ppm 7.91 (d, J=8.00 Hz, 2H), 7.31 (d, J=8.00 Hz, 2H), 3.04-3.09 (m, 1H), 2.57 (s, 3H), 2.35-2.55 (m, 4H), 2.07-2.17 (m, 2H), 2.07-2.11 (m, 1H), 1.77-1.90 (m, 1H); $^{13}$C NMR (101 MHz, CDCl$_3$) δ ppm 210.40, 197.75, 149.73, 135.83, 128.94 (2C), 126.93 (2C), 48.48, 44.70, 41.17, 32.49, 26.68, 25.49.

E)-7-Phenylhept-6-en-3-one (Entry 7, Table 2

Colorless liquid, $^1$H NMR (400 MHz, CDCl$_3$) δ ppm 7.28-7.37 (m, 4H), 7.21-7.24 (m, 1H), 6.43 (d, J=8.12 Hz, 1H), 6.19-6.26 (m, 1H), 2.63 (t, J=4.13 Hz, 2H), 2.45-2.54 (m, 4H), 1.10 (t, J=8.12 Hz, 3H); $^{13}$C NMR (101 MHz, CDCl$_3$) δ ppm 210.84, 137.51, 130.75, 129.10, 128.58 (2C), 127.15, 126.07 (2C), 41.92, 36.14, 27.28, 7.88.

E)-5-Phenylpent-4-enal (Entry 8, Table 2

Colorless liquid, $^1$H NMR (400 MHz, CDCl$_3$) δ ppm 9.83 (t, J=4.00 Hz, 1H), 7.27-7.34 (m, 6H), 7.19-7.23 (m, 1H), 6.43 (d, J=8.00 Hz, 1H), 6.17-6.24 (m, 1H), 2.62-2.66 (m, 2H), 2.53-2.58 (m, 2H); $^{13}$C NMR (101 MHz, CDCl$_3$) δ ppm 201.96, 137.32, 131.25, 128.67 (2C), 128.27, 127.37, 126.17 (2C), 43.46, 25.64.

Lastly, to examine the utility of the catalyst on a somewhat larger scale, the reaction of cyclohexenone with phenylboronic acid was performed on a 20 mmol scale and the product 2-phenyl cyclohexanone was isolated in identical yield (83%) to the small-scale reaction (Table 1, entry 5). Thus, the ligands described herein may have practical application in larger scale reactions.

Example 4

Recycling Catalyst from Hydroarylation Reactions

The polymer-supported phosphite used in the hydroarylation reactions of Example 3 is quite soluble in tetrahydrofuran, dichloromethane, and toluene (e.g., 60 mg/ml in toluene), but is insoluble in methanol. Thus, it is recovered quantitatively by simple precipitation with excess methanol and filtration. Also, it is important to note that the MeOH/H$_2$O cosolvent used in the hydroarylations was not enough to cause precipitation of the catalyst. In fact, the use of water as a cosolvent has a marked positive effect on the reaction yield; in the absence of protic cosolvent, the hydroarylation of cyclohexenone proceeds to only 35% conversion after 15 hours.

In this example the reaction of cyclohexenone and phenylboric acid was investigated. The reusability of the catalytic system was also examined up to five consecutive hydroarylation runs (as described in Example 3) and it was observed that filtration under air was associated with the gradual loss of catalytic activity with respect to yield of the product whereas filtration under schlenk system yielded no appreciable loss of catalytic activity for the subsequent runs. The results are shown in Table 3.

TABLE 3

| Catalyst Recycle | | | |
|---|---|---|---|
| Filtration under air | | Filtration under argon | |
| Run | Yield (%) | Run | Yield (%) |
| 1 | 83% | 1 | 83% |
| 2 | 83% | 2 | 83% |
| 3 | 85% | 3 | 82% |
| 4 | 73% | 4 | 82% |
| 5 | 68% | 5 | 83% |

Example 5

Batch Membrane Nano/Ultra-Filtration of Rhodium Complexes from Homogenous Organic Solutions In this example, membrane nano/ultra-filtration of designed polymer-bound Rh complex catalyst is demonstrated as an effective in situ catalyst recovery method for homogeneous hydroformylation reaction systems. Quantitative extents of recovery of the rhodium metal and phosphorus-based ligands were investigated in batch membrane filtration experiments with various soluble polymer bound rhodium complexes dissolved in toluene. ICP technique was explored for analyses of Rh and P in organic matrix.

Experimental Apparatus

The STARMEM® nano/ultra filtration membrane was distributed by Membrane Extraction Technology, UK and manufactured by W. R. Grace-Davison (USA). The membrane is made of highly cross-linked polyimide and asymmetric with the active side in contact with the solution to be filtered. This membrane rg has a diameter of 90 mm and an active surface area of 54 cm². The thickness of the active layer is less than 0.2 mm with a pore size less than 50 angstroms. The molecular weight cut-off (MWCO) of the membrane ranges from 200 to 400 Daltons, based on 90% retention of the solute. This membrane is compatible with most of the conventional organic solvents, such as alkanes, aldehydes, alcohols, and aromatics. Its durable rating is up to one year with a maximum operating temperature of 75° C.

The MET cell was purchased from Membrane Extraction Technology (MED) (London, UK) and made of 316 stainless steel. The flat paper-like membrane is placed at the bottom of the MET cell and supported by a porous sintered stainless steel disk, which provides mechanical strength to the membrane. Thus the membrane functions as a dead-end filter. The maximum working volume of the MET cell is 270 mL with a hold-up volume of 5 mL. Two inlets (one for feed and the other for pressurizing gas) enable continuous and air-free operation. The cell is equipped with Teflon-coated magnetic stirrer bar fixed on a metal bracket soldered to the top lid. The maximum operating pressure is 1000 psi (69 bars). This is a dead-end mode filter with a flat membrane sheet.

Figure 2:
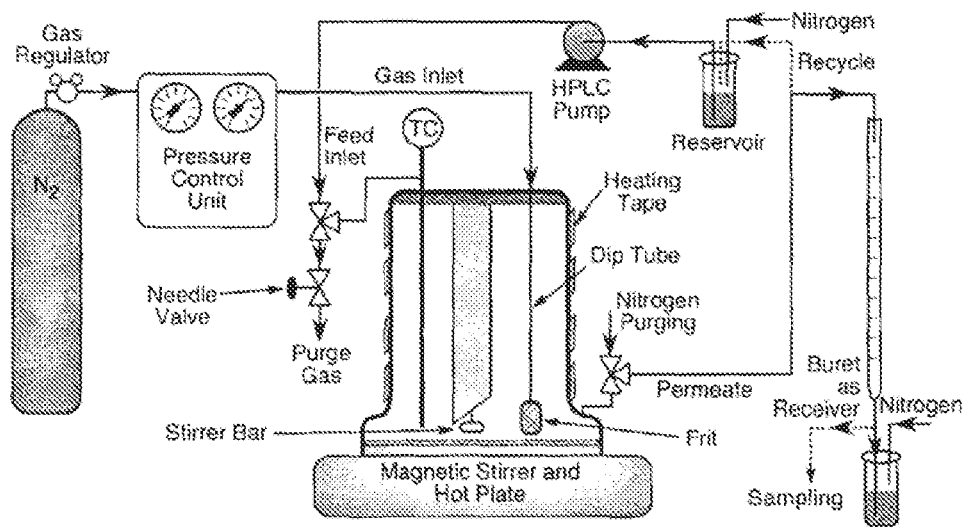
FIG. 2 shows the membrane filtration setup configuration as used in the examples.

FIG. 2 shows the schematic of the membrane filtration setup. The cell body is wrapped with a heating tape and insulation, and placed on a magnetic stirrer and hot plate (Barnstead Cimarec Stirrer with stirrer setting of 1-12 and stirrer speed range of 60-1200 rpm) for mixing and heating. A thermocouple, interfaced with LabView® data acquisition, measures the solution temperature. The solvent or the substrate is pumped into the cell at a constant flowrate ranging from 0.01 to 20 mL/min. Both the feed reservoir and permeate receiver are blanketed with inert nitrogen gas. This setup is capable of either batchwise or continuous filtration under air-free condition. There are a variety of inert gases that can serve as pressurizing gases. Nitrogen was used in the current example. $CO_2$ will also be used in future studies to create $CO_2$-expanded solvent media with lower viscosity. For performing homogeneous hydroformylation reactions with simultaneous filtration of the catalyst complex, either synthesis gas ($CO/H_2$=1:1 molar) or its mixture with $CO_2$ will be employed as the pressurizing gas. Following filtration, the cell pressure is released gradually via a regulating valve to avoid membrane doming caused by sudden pressure change. The permeate may be recycled back to the cell, with provisions for sample withdrawal for analysis purposes.

Catalyst Systems and Analytical Methodology

The homogeneous catalytic systems tested for filtration consist of the catalyst precursor $Rh(acac)(CO)_2$ (Rh-50) and various phosphorous ligands dissolved in toluene. Triphenylphosphine (TPPine) was used as the benchmark ligand with the lowest molecular weight. Biphephos and BiPhPhM bulky bidentate phosphite ligands were synthesized and supplied by the University of Kansas Department of Chemistry. The lettering protocol (a, b, and c) after the polymer supported ligands is used to designate different batches of polymer following the same synthesis procedure. The PDI for one PBB10 sample ws estimated to be 1.3, but it is anticipated that the PDI should not vary significantly from batch to batch. Table 2 provides the structures of all the phosphorous ligands and their molecular weights. The shaded circles represent the polymer backbone. Table 4 shows the catalysts systems investigated.

TABLE 4

Phosphorus Ligands and Their Molecular Weight

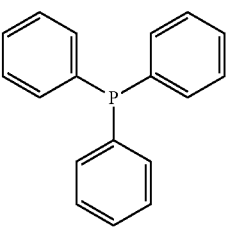 [SMILES: c1ccc(P(c2ccccc2)c2ccccc2)cc1]

TPPine, Mw = 262.29 g/mol

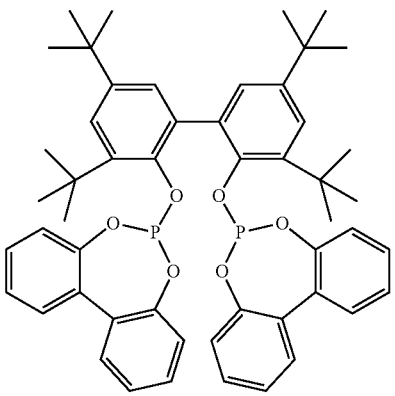 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1]

BiPhePhos, Mw = 838.94 g/mol

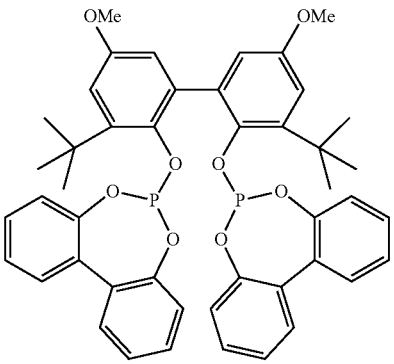 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

BiPhPhM, Mw = 786.78 g/mol

TABLE 4-continued

Phosphorus Ligands and Their Molecular Weight

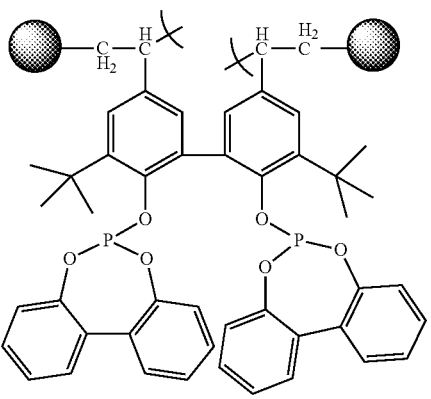 [SMILES: CCC(C)c1cc(-c2cc(C(C)CC)cc(C(C)(C)C)c2Op2oc3ccccc3c3ccccc3o2)c(Op2oc3ccccc3c3ccccc3o2)c(C(C)(C)C)c1]

PBB10a, b, c Mw = 10,000 g/mol

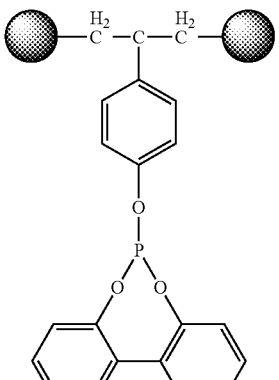

PBP10a, Mw = 10,000 g/mol

Catalyst solutions were prepared by dissolving known amounts of Rh(acac)(CO)$_2$ (Rh-50) and other ligands in toluene and leaving the stirred solutions in a glove box overnight to allow Rh binding. The solutions were blanketed by an inert gas during mixing, binding, and transferring. The starting or feed solutions containing the catalyst complex or ligands are designated as F. The solution passing through the membrane is called the permeate (designated as P) and the solution rejected by the membrane is called the retentate (designated by letter R).

The unmodified rhodium catalyst, Rh(acac)(CO)$_2$, designated as Rh-50, with a purity of 99% and the ligand, triphenylphosphine (PPh$_3$) with purity of 99%, were obtained from Alfa Aesar. Anhydrous toluene in Sure/Seal™ at purity of 99.8% was purchased from SigmaAldrich, Inc.

Inductively coupled plasma optical emission spectroscopy ("ICP-OES") was employed to quantify the rhodium and phosphorous concentrations in the starting catalyst solution, the retentate and the permeate. The ICP is an emission spectroscopic technique based on the principle that the intensity of the light emitted by excited ions is proportional to the respective elemental concentration in the analytical solution. The excitation energy is supplied by an electrical current produced by electromagnetic induction. The ICP is widely applied for elemental analyses in metallurgy, agriculture, biology, environment, and geological materials. In most cases, aqueous analysis is preferred after acid digesting the heterogeneous sample. In contrast, organic matrix analysis is rarely used due to the paucity of standards for organic matrix and their short shelf time. In this example, toluene was chosen as a solvent to accommodate phosphorous bound rhodium complexes, due to its strong solvation power for the catalyst complex and the hydroformylation reaction mixture.

The ICP instrument used in this work was a Jobin Yvon 2000 2 with radial plasma view and monochromator optical system. The liquid sample solution is introduced by peristaltic pump and then sprayed and converted to aerosols by Meinhard concentric nebulizer. The aerosols are sorted by the cyclonic spray chamber and only droplets smaller than 10 µm reach the torch and plasma. It should be noted that only a small quantity of sample aerosols is allowed so as to keep the plasma from being extinguished. The radio frequency generator supplies energy for sustaining the plasma and produces a high-frequency electromagnetic field in the induction coil with output power of between 800 to 1500 W at a frequency of 40.68 MHz. Inside the high temperature plasma, the aerosols carried by argon gas are preheated to dryness and then excited by the ionized gas to high-energy atoms and ions. After passing the radiation zone, these particles release the energy in the form of photons at certain frequencies or wavelengths. Each element has its own characteristic emission lines. The principles of atomic emission, operating safety, matrix selection, and maintenance are detailed in the manufacturer-supplied manuals "User Manual Jobin-Yvon ICP Spectrometers" and "User Manual ICP V5 Software."

Calibration standards were made by dissolving Rh(acac)(CO)$_2$ and triphenylphosphine ("TPPine") in toluene. Toluene was also used to dilute the samples and calibration solutions to lower the viscosity of the sample solutions and reduce its influence on the results. The calibration graphs showed excellent linearity for both Rh and P spanning several orders of magnitude down to ppb level. For example, dissolved Rh can be detected quantitatively at concentrations as low as tens of ppb. Appendix III provides relevant details for ICP method development, calibration procedure, analysis protocols, and operation.

Experiment Procedure: Pre-Conditioning and Flux Measurements

Prior to filtration, the membrane was conditioned by flushing pure toluene through it under nitrogen pressure of 3.0 MPa for one hour. The permeate from this conditioning run was disposed of because of contamination of the solvent with membrane lubricating preservative oil. Following the preconditioning step, the flushing was continued with fresh toluene that was continuously circulated back to the cell. This step was continued till the flux (mL toluene/min) through the membrane leveled out, signaling membrane equilibration. The equilibration step normally takes about three days. After these pretreatment steps, the membrane was ready for the nanofiltration studies of the solution containing dissolved catalyst complexes. Between each filtration run, the membrane was washed three times and soaked overnight in toluene.

During each filtration run, the permeate fluxes were periodically recorded to ensure constant rate throughout the filtration process thereby eliminating any variations due to physical damage to the membrane (i.e., cracking, clogging, and other defects on the membrane surface). Further, a blank filtration run with pure toluene was carried out before and after each filtration with the solution containing dissolved catalyst complex. Under identical gas pressures, lower fluxes were typically observed for the runs with dissolved compared to pure toluene. This is attributed to the increased viscosity of the catalyst solution containing dissolved polymer supports.

The permeate volume was measured in a 100 mL burette of which the ungraduated bottom part was calibrated as 5.5 mL. The accuracy of the burette is ±0.2 mL. A stopwatch with an accuracy of ±1 s was used to record the time for collecting certain volumes of permeate. The transient permeate flux is represented by the average flux in a small period of time, in a form of $$J = \frac{\Delta V}{A \Delta t},$$

where J is the membrane flux ($L \cdot m^{-2} \cdot hr^{-1}$), $\Delta V$ is the permeate volume (L), $\Delta t$ is the period of time (hours) and A is active membrane surface area ($m^2$), equal to 54 $cm^2$ specified by the manufacturer. Another parameter characterizing the membrane flux is the membrane permeability, a normalized transient permeate flux to pressure ratio with a unit of $L \cdot m^{-2} \cdot hr^{-1} \cdot bar^{-1}$.

Batch Filtration Experimental Procedure

To begin the batch filtration, the catalyst solution is transferred via air-tight syringe into the MET cell through the feed inlet with concurrent nitrogen purging at low pressure of a few psi. The typical volume of the initial solution is 60 mL. Then the cell is pressurized with nitrogen to the desired pressure (1.0 MPa). The cell pressure is maintained constant by replenishing the dissolved gas that escapes through the membrane with fresh nitrogen from a source gas cylinder. The magnetic stirring rate is set at 4 out of 0-12, and the 100 mL burette permeate receiver is purged with nitrogen. The filtration is commenced by opening the permeate valve and allowing the cell contents to be filtered through the membrane until half of the initial volume is collected as permeate. The permeate flux is calculated by timing the volumetric flow with the 100 mL burette placed in the effluent. After the desired amount of permeate is collected, the permeate check valve is shut off to stop filtration. The retentate and permeate streams are then sampled for Rh and P elemental analysis by ICP. The foregoing procedural steps were all done at room temperature (about 21° C.). Then the MET cell is transferred into a glove box and the retentate is collected after washing three times and overnight soaking. Before reusing the membrane, a visual check and flux measurement are made to ensure that the membrane is in good condition.

The metal pass-through was calculated as follows:

$$\text{Pass-through} = \frac{\text{total } Rh \text{ or } p \text{ in permeate}}{\text{total } Rh \text{ or } P \text{ in starting solution}}$$

Batch Filtration Experimental Results

The three polymer supported ligands (PBB10a, PBB10b and PBB10c) as well as one bidentate ligand (BiPhPhM) were tested. The P-loading was 0.949, 0.634, and 0.645 mmol/g for the three batches investigated (PBB 10a, 10b, 10c, respectively), respectively. The catalyst solution contain rhodium and phosphorous at concentrations ranging from 70-110 ppm and 90-300 ppm respectively with rh a molar P/Rh ratio of 4 to 8 as provided in the Table 5.

TABLE 5

Catalyst and ligand compositions in the initial catalyst solutions in each run

| Ligands | Runs | [Rh] µg/g (ppm) | [P] µg/g (ppm) | P/Rh molar |
|---|---|---|---|---|
| PBB10a | 1st Run | 109.20 | 266.23 | 8.1 |
| PBB10a | 2nd Run | 87.18 | 211.46 | 8.1 |
| PBB10b | 1st Run | 101.76 | 218.24 | 7.2 |
| PBB10b | 2nd Run | 97.07 | 208.18 | 6.9 |
| PBP10a | 1st Run | 83.11 | 98.37 | 4.0 |
| PBP10a | 2nd Run | 80.38 | 95.15 | 4.0 |
| BiPhPhM | Run1 | 68.80 | 181.20 | 8.8 |
| BiPhPhM | Run2 | 79.69 | 189.99 | 8.0 |

All filtrations and flux measurements were run at room temperature (21° C.). The permeate flux were measured before and after each filtration with pure toluene as blank run to check repeatability of the membrane flux so as to ensure the membrane in good condition. Table 6 provides membranes and nitrogen pressures used for each run.

TABLE 6

Membrane, permeate flux and nitrogen pressure used in each run

| | Membrane | Flux, L/(m² hr) (nitrogen pressure, MPa) | | | |
|---|---|---|---|---|---|
| Ligands | MWCO Daltons | Before (pure toluene) | $1^{st}$ filtration | After (pure toluene) | $2^{nd}$ filtration |
| PBB10a | 400 | 70 (2.0) | 23 (1.0) | 55 (2.0) | 24 (1.0) |
| PBB10b | 200 | 32 (3.0) | 12 (1.0) | 34 (3.0) | 13 (1.0) |
| PBP10a | 200 | 19 (3.0) | 7 (1.0) | 20 (3.0) | 6 (1.0) |
| BiPhPhM | 200 | 17 (3.0) | 7 (1.0) | 23 (3.0) | — |
| BiPhPhM | 200 | 19 (3.0) | 6 (1.0) | 22 (3.0) | — |

Figure 3:
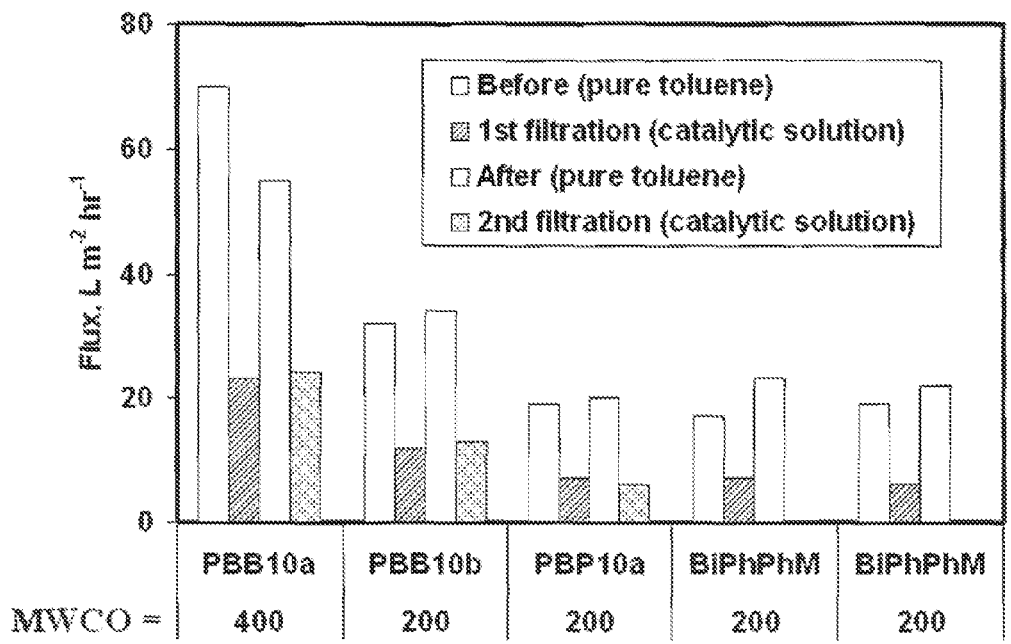
FIG. 3 shows the permeate fluxes before, during, and after each filtration of catalytic solutions containing each ligand. Filtration conditions: T=21° C. and under constant nitrogen pressure of 1.0 MPa; about half of the initial catalyst solution was filtered in each case.

FIG. 3 shows the permeate flux attained in various filtration runs performed with different solutions and different membranes. The white bars represent the blank filtration runs with pure toluene only while the hatched and dotted bars represent the first and second filtration runs respectively performed with solutions containing dissolved catalyst complexes. As expected, pure toluene with lower viscosity yields higher permeate fluxes compared to the catalyst solutions, at a constant gas pressure.

For each of the three polymer supported ligands PBB10a, PBB10b and PBB10c, two consecutive runs performed with the same membrane yielded nearly identical permeate fluxes confirming, the stability of the membrane. For the bidentate ligand (BiPhPhM), two repeated runs each were performed on two different membranes. These fluxes were reproducible as well.

Figure 4:
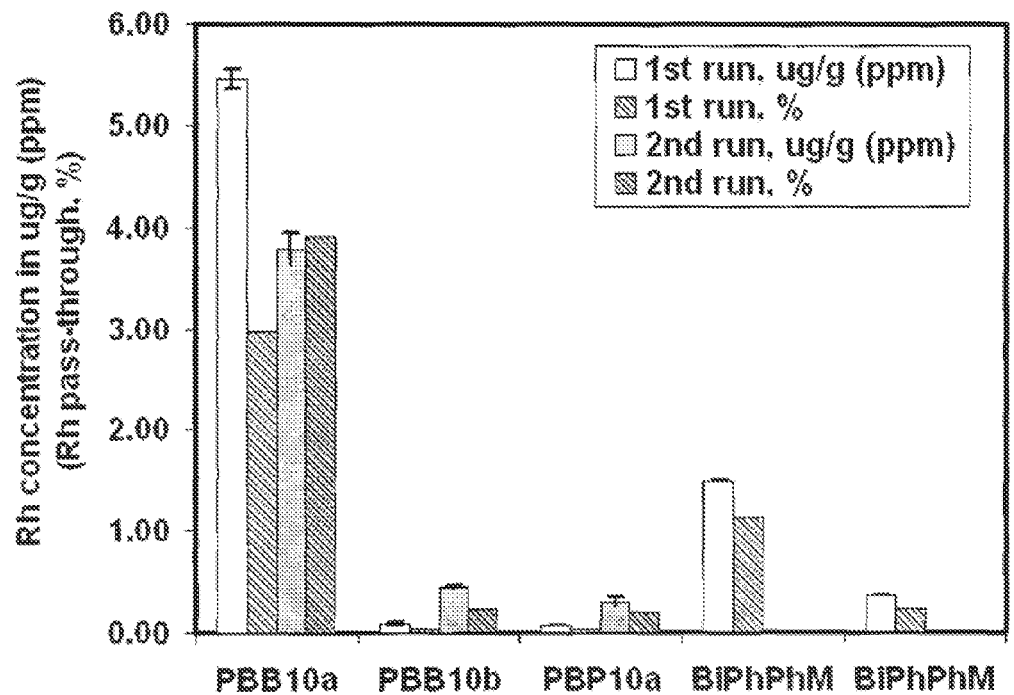
FIG. 4 shows the rhodium concentrations in permeate and the Rh pass-through for batch filtrations of solutions containing various dissolved catalyst plus ligand combinations. Filtration conditions: T=21° C. and under constant nitrogen pressure of 1.0 MPa. About half of the initial catalyst solution was filtered in each case. Initial catalyst solution: volume=40-60 mL, [Rh]=70-110 ppm, [P]=90-300 ppm, molar P/Rh ratio=4-8.
Figure 5:
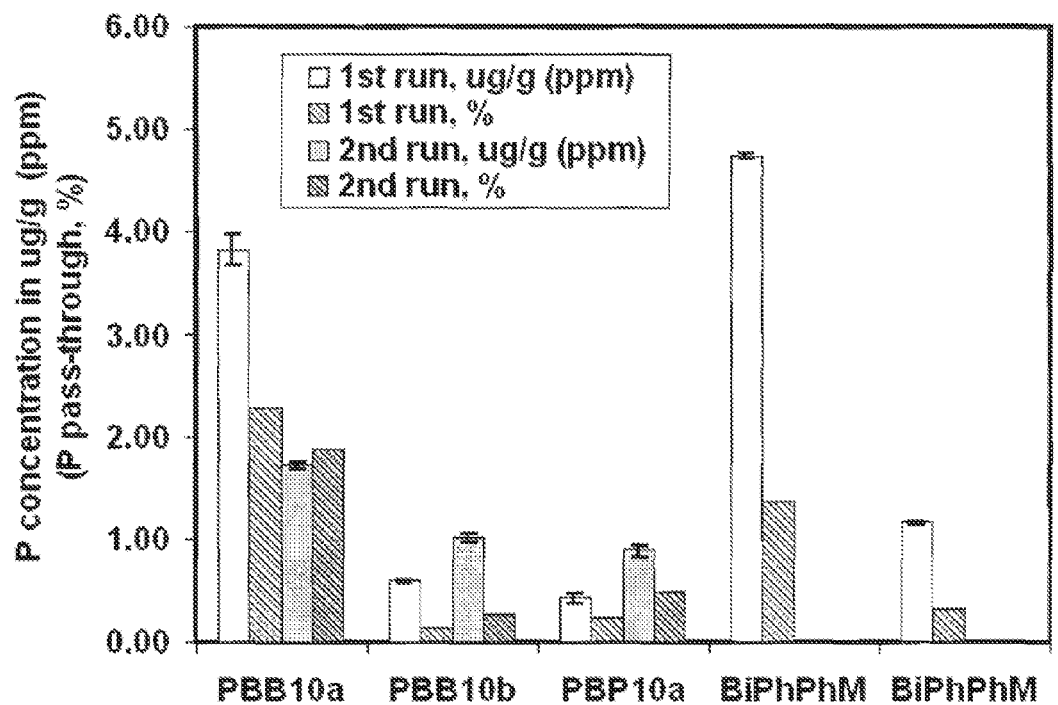
FIG. 5 shows the phosphorous concentration in permeate and the Rh pass-through for each catalytic solution containing different ligands. Filtration conditions: T=21° C. and under constant nitrogen pressure of 1.0 MPa; about half of the initial catalyst solution was filtered in each case. Initial catalyst solution: volume=40-60 mL, [Rh]=70-110 ppm, [P]=90-300 ppm, molar P/Rh ratio=4-8.

FIG. 4 and FIG. 5 give the ICP-measured Rh and P concentrations in the permeate stream for each batch run. The metal pass-through was calculated as follows:

$$\text{Pass-through} = \frac{\text{total } Rh \text{ or } p \text{ in permeate}}{\text{total } Rh \text{ or } P \text{ in starting solution}}$$

For the PBB10a ligand, the Rh concentrations in the permeate are approximately 5.5 µg/g (ppm) and 3.8 µg/g (ppm) in the first and second runs, respectively. The Rh pass-through estimates are approximately 3% and 4%, based on filtration of half of the initial solution volume. The rather high pass-through values are attributed to the larger pores in the higher MWCO membrane. They could also be due to either incomplete membrane equilibration and/or impurities in the polymer that degrade the membrane surface.

For the PBB10b and PBP10a ligands, the two first runs at constant membrane flux rates yield significantly low Rh pass-through values, on the order of a few tens of ppb. The second run yielded a somewhat higher rhodium concentrations in the permeate, albeit still at ppb levels.

For the bidentate ligand (BiPhPhM), Rh concentrations in the permeate are higher as expected, compared to those for the polymer supported ligands (PBB10b and PBP10a), which is attributed to the almost 10 fold smaller size of the non-polymer supported ligand and complex. FIG. 5 shows the same trends of P concentrations in permeate as Rh. Polymer supported ligands (PBB10b and PBP10a) yield the lowest P concentrations in the permeate and correspondingly lowest pass-through values, in the permeate.

Example 6

Continuous Homogenous Hydroformylation of 1-Octene with In Situ Membrane Filtration This example deals with continuous membrane filtration coupled with hydroformylation reaction at elevated temperature and pressure to determine whether steady operation characterized by constant flux, stable substrate conversion and selectivity can be demonstrated for extended periods. The soluble polymer ligands that displayed the best retention properties during the batch and continuous filtration runs described in Example 5 were employed in the investigations under the conditions of hydroformylation.

Continuous Membrane Filtration Experimental Procedure (without Reaction)

For the continuous filtration, all the membrane and sample preparation procedures are the same as the batch runs described above. The main difference is that pure toluene is pumped continuously into the cell by means of an HPLC pump at a predetermined flow rate such that the liquid volume in the cell is maintained constant during filtration. A metering valve in the effluent stream is used to ensure that the feed and permeate flow rates are maintained constant. Permeate samples are withdrawn periodically for analysis. When running at elevated temperatures, the cell is preheated and the temperature of the cell contents is stabilized before filtration is commenced.

Continuous Membrane Filtration Experimental Procedure (with Reaction)

A substrate solution of toluene and 1-octene (v/v=70:30) was prepared. After installing the membrane in the reactor, it was conditioned and equilibrated with anhydrous toluene under a nitrogen pressure of 3.0 MPa.

A 60 mL solution of $Rh(acac)(CO)_2$ and polymer bound ligand in toluene was injected via syringe into the MET cell under a nitrogen atmosphere. The mixture was stirred while repressurizing the system with syngas and raising the temperature to 60° C. The feedstock pump was started at a flowrate of 0.1-0.5 mL/min, while simultaneously opening the permeate valve slowly and adjusting the permeate flow rate to the same value as that of the feed. The flowrate in this range ensures that the substrate has adequate residence time (at least 120 minutes) in the catalytic reactor. Every hour, a sample was taken from the permeate stream. One small portion of this sample was diluted with dichloromethane, and analyzed by gas chromatography Varian GC 5800 (CP-Si15CB Chromapack® capillary column). The other portion of this sample was analyzed by ICP JY 2000 2 for Rh and P analyses.

Each run was terminated by shutting down the syngas supply and closing the feed and permeate valves. However, reaction would still continue inside the membrane reactor until it reached equilibrium. This is signified by a drop in syngas pressure, sometimes down to zero when the substrate 1-octene was in excess. Continuous operation is resumed by re-establishing syngas and feedstock flows, and by opening the permeate valve. The conversion versus time profile exhibited a rising profile during the start-up stage and then reached a steady state.

Continuous Membrane Filtration without Reaction: Results

Two repeated filtration runs were performed using toluene-based solutions containing dissolved polymer supported ligand (PBB10c) with two fresh membranes (MWCO of 200 Daltons). The catalyst solutions contain Rh and P at concentrations ranging from 100-150 ppm with a molar P/Rh ratio of 4.

Figure 6:
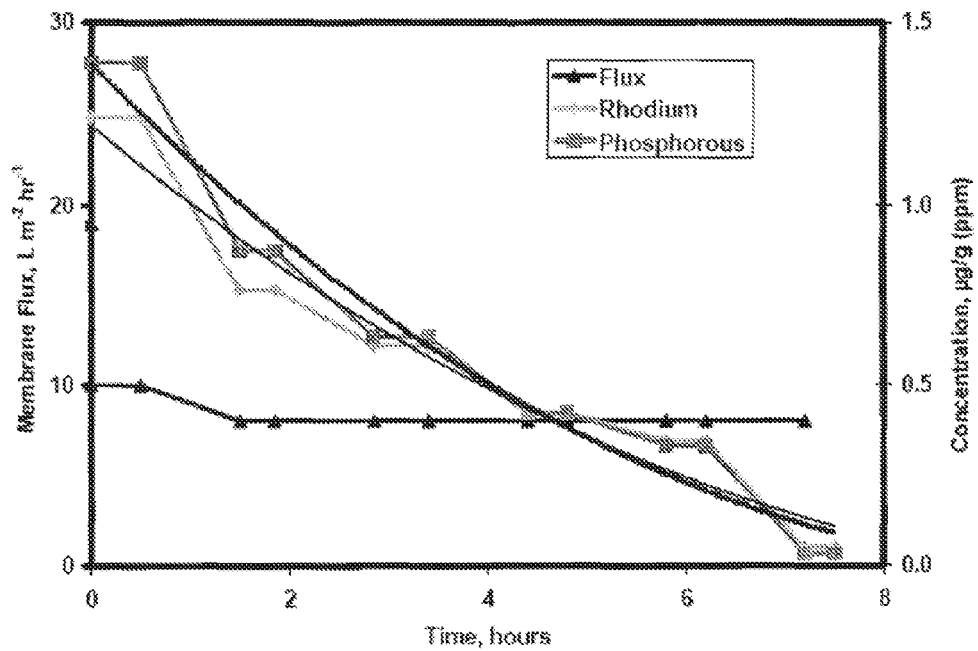
FIG. 6 shows the membrane flux, rhodium and phosphorous concentrations in permeate for the first continuous filtration run. Filtration conditions: T=21° C., under nitrogen pressure of 1.0 MPa. Initial catalyst solution: [Rh]=121 ppm, [P]=144 ppm, molar P/Rh ratio=4

The first continuous filtration run shown in FIG. 6 lasted for 7.5 hours. The permeate flux during the entire run remained constant at 8 L $m^{-2}$ $hr^{-1}$, which is approximately 40% of the flux attained with pure toluene at identical cell pressures. The Rh and P concentrations in the effluent were high initially and decreased with time suggesting the removal of perhaps unbound Rh and P from the initial mixture and also from the fraction of the polymers that are lighter than the MWCO of the membrane. The Rh and P concentrations lined out at ppb levels (about 50 ppb) after several hours. Total losses of Rh and P during the line-out duration are 2.1% and 1.9% respectively, obtained by integrating the area under the empirically fitted concentration vs. time curves. This means that about 98% of the Rh and P were retained in the cell. Assuming that the Rh and P leaching is substantially complete during the line-out period and remained at these values, the targeted rhodium recovery rate 99.8% per pass is easily achieved beyond the line-out period.

Figure 7:
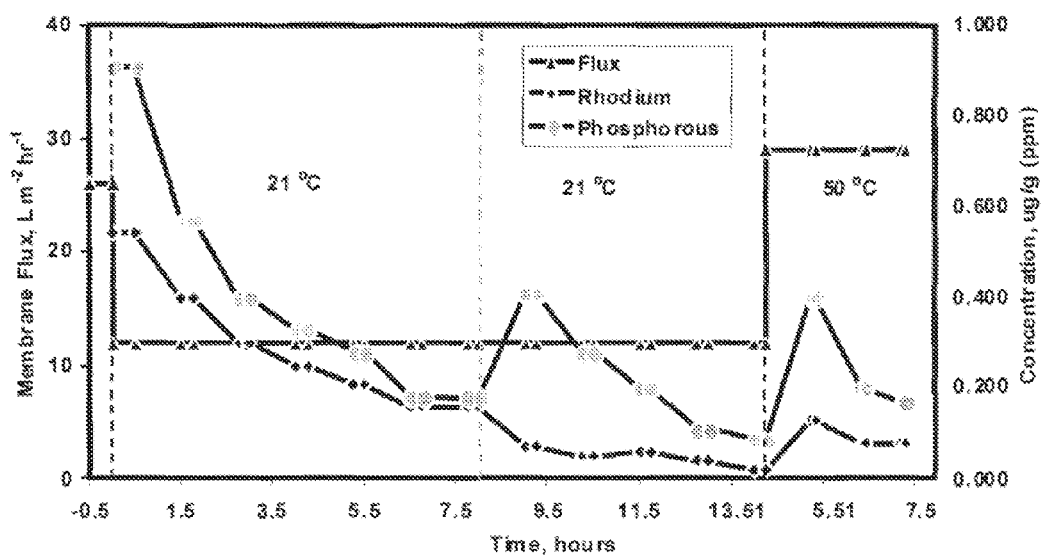
FIG. 7 shows the membrane flux, rhodium and phosphorous concentrations in permeate for the second continuous filtration run. Filtration conditions: T=21° C., under nitrogen pressure of 1.0 MPa. Initial catalyst solution: [Rh]=117 ppm, [P]=142 ppm, molar P/Rh ratio of 4. During the downtimes, the catalyst solution was sealed in the MET cell under nitrogen pressure of 1.0 MPa.

FIG. 7 shows the permeate flux along with the Rh and P concentrations in the permeate versus time for the second continuous filtration run. This filtration run lasted for 17 hours in total, and was performed in three stages as follows. The first stage (the first 8 hours) represents a repeat of the first continuous run. After two weeks following this run, during which the cell contents were maintained in nitrogen atmosphere at a constant pressure, the filtration was resumed and continued for another 6 hours. Similar to the first run, the permeate flux remains constant. The Rhodium and phosphorous concentrations in permeate decreased down to 20 ppb and 90 ppb respectively after 14 hours of filtration. Total losses of Rh and P during the line-out period are 1.9% and 2.6% respectively obtained by integrating the area under the empirically fitted concentration versus time curves. The Rh and P losses are similar to those obtained during the line out phase of the first run.

In order to test the temperature effects, the filtration of the previous cell mixture (filtered for 14 hours at room temperature) was continued after two weeks, heating the cell to 50° C. The higher Rh and P concentrations in the permeate following line-out is attributed to the approximately 2.5 times greater membrane flux, due partly to the lower mixture viscosity at higher temperature. However, the Rh concentration is still at tens of ppb levels.

The P concentration curve exhibits a spike at the beginning of each continued run. This is attributed to the flushing of the Rh and P that may have accumulated in the hold-up volume (under the membrane assembly) by slow diffusion across the membrane during the two weeks. When the filtration resumes, the accumulated Rh and P are first washed out before the profiles line out again at previously attained values (tens of ppb levels), as shown in FIG. 7.

Continuous Membrane Filtration with Reaction: Results

The continuous experiment for 1-octene hydroformylation catalyzed by PBB 10d modified rhodium complex was carried out at temperature of 60° C. and under syngas pressure of 0.6 MPa. The solution was kept stirred at a setting that is equivalent to 1000 rpm. The Rh and P concentrations in the initial solution are 139 ppm and 184 ppm, respectively. The molar P/Rh ratio is 4.4.

Figure 8:
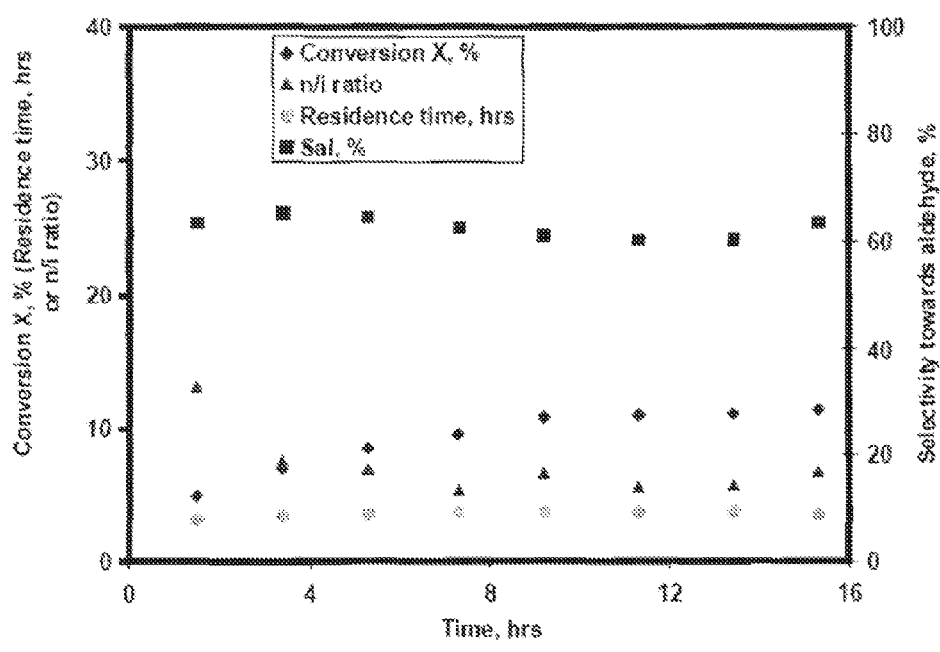
FIG. 8 shows the experimental results for continuous 1-octene hydroformylation with in situ membrane.

As shown in FIG. 8, the conversion slowly increases during the first 8 hours of the initial run and then remains at 11% for the following 8 hours while the residence time is kept constant at 3.5 hours. The regioselectivity n/i ratio decreases from 13 for the first sample down to 6 at the end of the 15-hour run. The selectivity towards aldehyde product reaches a steady value in the range of 60-65%, with relatively less variation.

Figure 9:
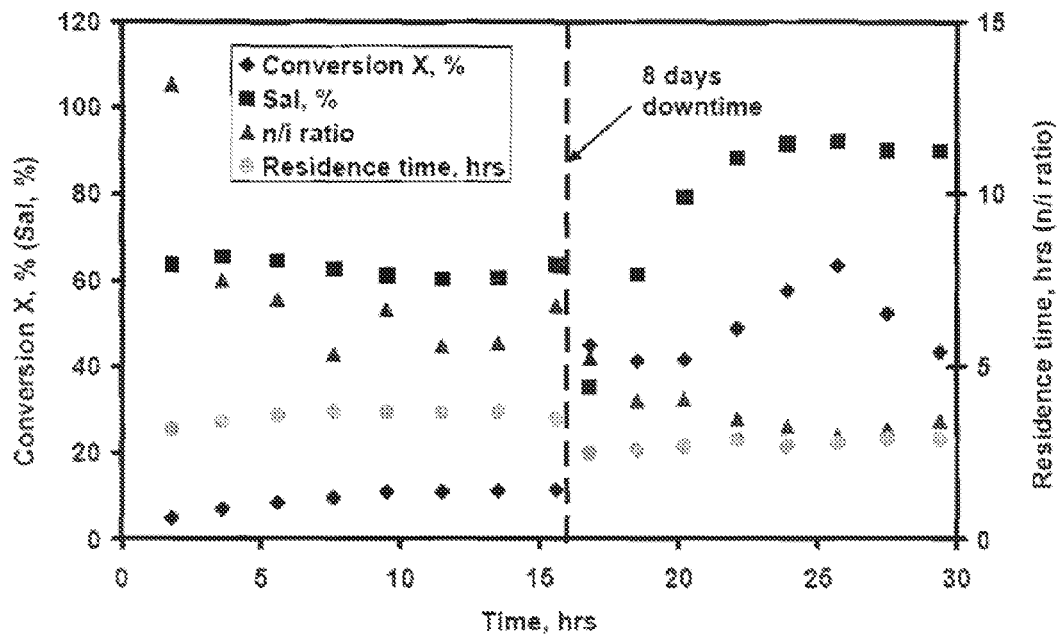
FIG. 9 shows the experimental results for continuous 1-octene hydroformylation with in situ membrane at different syngas pressures. Experimental conditions: T=60° C., constant syngas pressures, P=0.6 MPa for the first 15 hours and P=2.0 MPa for the second 15 hours, ligand: PBB10d; Initial catalyst solution: [Rh]=139 ppm, [P]=184 ppm, molar P/Rh ratio=4.4. At the end of the first 15-hour run, the catalyst solution was sealed in the MET cell. The reaction continued and the catalyst solution containing excess 1-octene would eventually be in a syngas starved environment.

After sealing the reaction mixture for 8 days in the reactor at the same stirrer speed as the previous reaction, the continuous run was resumed at a higher syngas pressure (2.0 MPa) for another 15 hours, with an average residence time of approximately 3 hours. The purpose of this run was to investigate the effect of syngas partial pressure on conversion and selectivity. As inferred from FIG. 9, the reaction under 2.0 MPa syngas gives higher conversion (greater than 40%) and higher selectivity to aldehydes (greater than 90%), compared to the run under 0.6 MPa syngas. In contrast, the n/i ratio gradually decreases from 6 down to 3.5.

Figure 10:
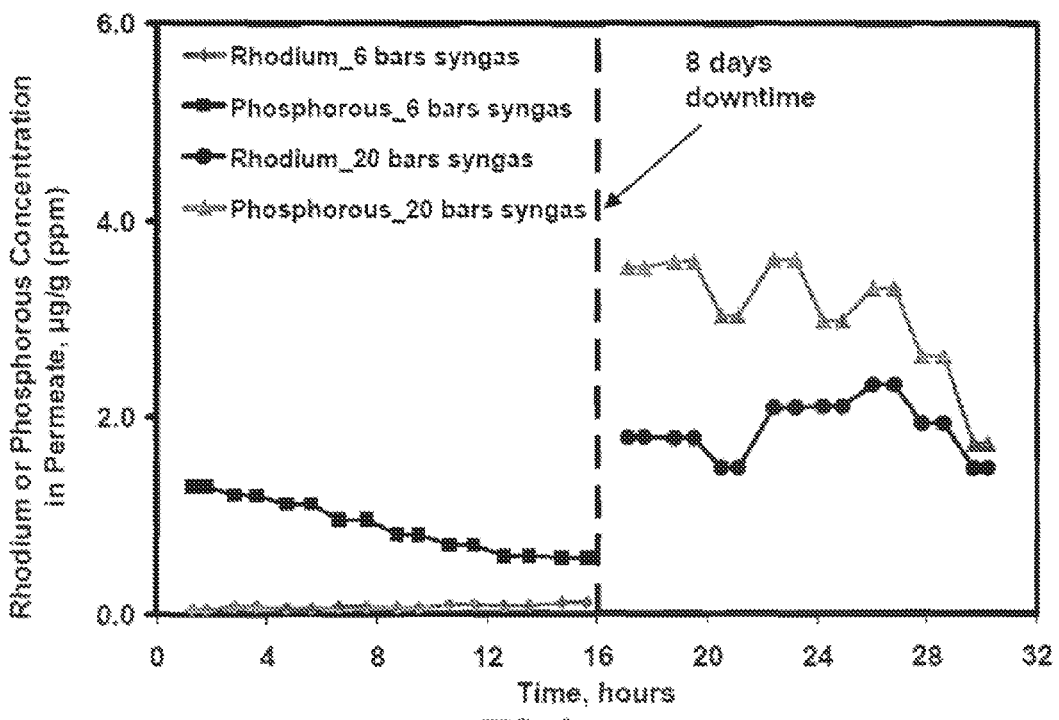
FIG. 10 shows the Rh and P concentrations in permeate for the two consecutive continuous 1-octene hydroformylation runs at different syngas pressures. Experimental conditions: T=60° C., constant syngas pressures, P=0.6 MPa for the first 15 hours and P=2.0 MPa for the second 15 hours, ligand: PBB10d; Initial catalyst solution: [Rh]=139 ppm, [P]=184 ppm, molar P/Rh ratio=4.4. At the end of the first 15-hour run, the catalyst solution was sealed in the MET cell. The reaction continued and the catalyst solution containing excess 1-octene would eventually be in a syngas starved environment.

The ICP analysis for the Rh and P concentrations in the permeate in the two consecutive continuous runs at different operating conditions is shown in FIG. 10. The first continuous run at 0.6 MPa syngas gives Rh contents in permeate lower than 120 ppb during the 15-hour run and P contents decreasing from 1.3 ppm to 570 ppb due to the pass-through of smaller size of polymer bound ligand.

The Rh and P levels from the second continuous run at 2.0 MPa syngas pressure are at low ppm levels. The reason for the increased pass-through is not clear at this time but it was observed that following the second continuous run, the retentate color (dark red) was completely different from that of the retentate for the batch runs (yellow). It is speculated that rhodium dimer was formed during the idle time between the two consecutive runs in the syngas starved environment and at the elevated temperature 60° C. The rhodium dimer formation reported often occurs at low pressures of hydrogen and high rhodium concentrations. The color changes can be associated with the reactions as follows where the ligand is triphenylphosphine (PPh3):

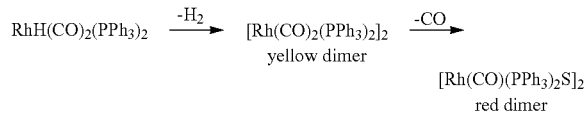

The same type of reactions might also occur when polymer bound ligand is used. The binding between the resulting rhodium dimer and the polymer bound ligand PBB10 might be weak, thus causing high Rh leaching through the membrane due to the smaller size of the dimer than the PBB 10 rhodium complex.

While the first 8 hours of the continuous experiment yielded steady 1-octene conversion and product selectivities, the actual values of these quantities are much lower than those attained during the batch experiments. It was suspected that this was due to a lack of vigorous mixing in the MET cell as received. That is, inadequate mixing would result in "syngas starvation" in the liquid phase which is known to adversely affect both conversion and product selectivity. To improve the mixing, the MET cell was fitted with a magnetically driven agitator that provided much better agitation of the liquid phase. The results are provided in the following second example.

Continuous Membrane Filtration with Reaction: Results (Second Example)

In a related example, the continuous experiment for 1-octene hydroformylation catalyzed by PBB 10d modified rhodium complex was carried out at temperature of 50° C. and under syngas pressure of 3.0 MPa. The solution was kept stirred with the new agitator at a setting that is equivalent to 1000 rpm. The Rh and P concentrations in the initial solution are 241.6 ppm and 400.4 ppm, respectively. The molar P/Rh ratio is 5.6.

Figure 11:
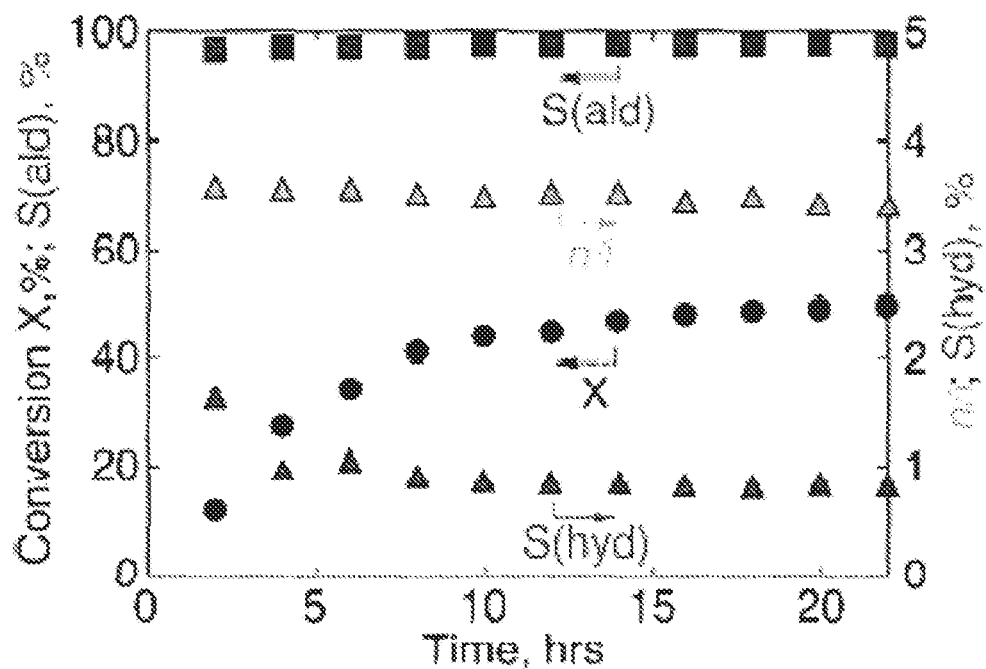
FIG. 11 shows the experimental results for continuous 1-octene hydroformylation with in situ membrane. Experimental conditions: T=50° C., constant syngas pressures, P=3.0 MPa, ligand: PBB10d; Initial catalyst solution: [Rh]=241.6 ppm, [P]=400.4 ppm, molar P/Rh ratio=5.6.

As shown in FIG. 11, the conversion slowly increases and reached a steady state after 8 hours around 50%. The regioselectivity n/i ratio remained constant about 3.0 to 3.5. The selectivity towards aldehyde product reaches a steady state value in the range of 90% or above, and was typically greater than 95%. The improved conversion and selectivity values prove that adequate mixing in the membrane reactor is important for achieving the desired conversion and selectivities.

Figure 12:
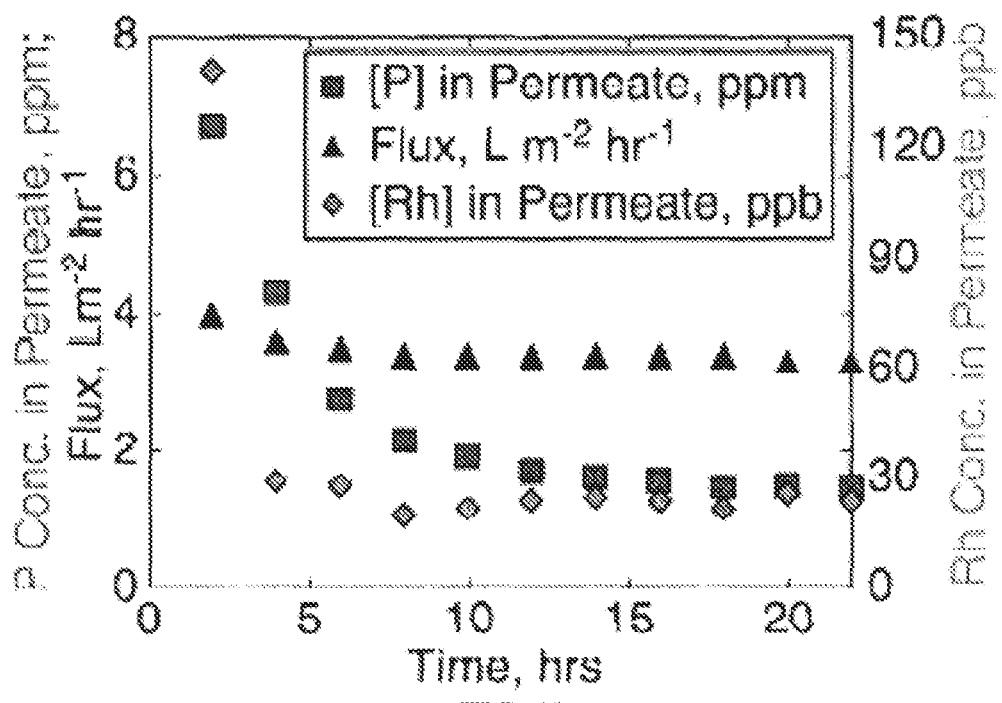
FIG. 12 shows the Rh and P concentrations in permeate for the continuous 1-octene hydroformylation runs shown in FIG. 11.

The ICP analysis for the Rh and P concentrations is shown in FIG. 12. Both concentrations reach a steady value in the permeate after 8 hours. The flow rate through the membrane was nearly constant throughout the 22 hour run suggesting that the membrane was not fouled. The Rh contents in permeate was lower than 140 ppb and were less than 30 ppb from 8 to 22 hours. The P content in the permeate decreasing from 6.7 ppm to 1.5 ppm due to the pass-through of smaller size of polymer bound ligand. The total losses of Rh and P during the 22 hour run were 0.08 wt % and 3.43 wt %.

Example 7

Batch Hydroformylation of 1-Octene Using Catalyst Composition

In this example, the hydroformylation of 1-octene was investigated using the catalyst composition of the present invention in which compressed carbon dioxide was utilized to volumetrically expand the liquid phase. In a stainless steel high-pressure reactor with thick-walled glass window and magnetic stirring bar, [Rh(acac)(CO)$_2$ (2.6 mg, 0.01 mmol) and polymer (Rh/P=1/3) were dissolved in toluene (3.6 ml) under inert atmosphere. The solution was stirred overnight at 25° C. and the solution turns to a yellowish color. After the addition of 1-octene (1.5 ml, 10.0 mmol) under an inert atmosphere, the reactor was charged with syngas (CO: H$_2$, 1:1 v/v). The reactor was heated with a thermo-coil wrapped on it. After achieving 60° C. (takes about 12 minutes), the reaction mixture was flushed five times with syngas and maintained at a constant syngas pressure at 6 bar. After two hours, the reaction mixture was cooled to room temperature and depressurized by the slow release of syngas inside an efficient fume cupboard. Then the reaction mixture was collected and 5 times of methanol was added to it. The white catalyst precipitate was separated quantitatively by filtration and reused for the subsequent runs after washing and drying. The product was analyzed by GC and the linear/branched aldehydes ratio was determined from the integral values of $^1$H NMR spectroscopy.

The same experiment was performed in $CO_2$-expanded liquid system also. In that case, the reactor was pressurized with $CO_2$ (32 bar) and left for one hour to attain equilibrium at 60° C. The syngas pressure was 6 bar (total pressure 38 bar). The results are shown in Table 7

TABLE 7

Comparison of Toluene vs. Carbon Dioxide Expanded Medium

| Expt. | Time (h) | Temperature (° C.) | Conversion (%) | TOF | Aldehyde (%) | Octane (%) | l/b |
|---|---|---|---|---|---|---|---|
| 1* | 2 | 60 | 93.4 | 467 | 85.7 | 1.1 | 2.1 |
| 2** | 2 | 60 | 91.7 | 458 | 82.2 | 1.2 | 7.9 |

*Reaction was carried out with toluene.
**Reaction was carried out with $CO_2$ expanded medium with toluene.

Example 8

Viscosity and Cloud Point Measurements

The dissolved polymer bound phosphite ligands discussed herein, used to facilitate better catalyst retention, could significantly increase the viscosities of hydroformylation reaction mixtures, especially at high concentration. When $CO_2$ is added into the organic solvent (toluene in this case), the organic solvent expands and the physical properties of the $CO_2$-expanded solvent are altered with $CO_2$ pressure. This is generally described in Jin et al., *Intensification of catalytic olefin hydroformylation in $CO_2$-expanded media*, AIChE Journal 52 (7) 2575-2581 (2006); Jin et al., *Homogeneous catalytic hydroformylation of 1-octene in $CO_2$-expanded solvent media*, Chemical Engineering Science 59 4887-4893 (2004), and Subramaniam et al. U.S. Pat. No. 7,365,234, which are all incorporated by reference.

Permeate flux is a key parameter for membrane filter throughput prediction, sizing and its capital cost estimation. In case that no significant concentration gradient is present in the porous membrane, the Hagen-Poiseuille equation was used to correlate solvent flux and viscosity for polyimide membranes.

$$J = \frac{\varepsilon r_p^2}{8\eta\tau} \cdot \frac{\Delta P}{\iota} = \frac{\varepsilon r_p^2}{8\tau\iota} \cdot \frac{\Delta P}{\eta}$$

where J is volume flux for solvent [m³ m⁻² s⁻¹], $\Delta P$ is the pressure drop across the membrane [Pa], $\eta$ is solution viscosity [kg (m s)⁻¹], $\varepsilon$ is membrane porosity, $r_p$ is membrane pore radius [m], $\tau$ is tortuosity, $\iota$ is membrane thickness [m]. See P. Vandezande et al., *Solvent resistant nanofiltration: separating on a molecular level*, Chemical Society Reviews 37 365-405 (2008). Solvent flux J increases with increasing pressure drop across the membrane and with decreasing viscosity. Obviously, viscosity is the only solution parameter that affects the solvent flux besides all other membrane parameters. The membrane pore size might change with the type of organic solvent used due to different swelling of membrane polymer. In addition, concentration polarization and non-ideality of solution are not considered herein.

The dissolution of $CO_2$ in organic solvents reduces the viscosities and increases the diffusivities of the organic solvents. Compared with other inert gases like nitrogen, $CO_2$ could not only serve as a pressurizing gas, but also as a reagent to tune the viscosities of the organic mixtures. Viscosity measurements of organic mixtures with various phosphorous ligands dissolved in toluene at different $CO_2$ pressures and temperatures will provide the evidence for the $CO_2$ tuning ability.

The viscosity measurements were performed in a ViscoPro 2000 System 4 with SPL-440 high pressure viscometer and Viscolab software, supplied by Cambridge Applied Systems (currently Cambridge Viscosity). The whole experimental setup consists of an air bath unit, feed pump, and $CO_2$ supply system. To obtain a uniform temperature environment, the air bath, which houses Jerguson view cell, circulation pump and viscometer, is controlled by a digital controller Yamato constant temperature oven DKN400. The Jerguson viewcell is rated to 5000 psi and has a total sample volume of 30 mL. With the equipped Jerguson viewcell, cloud point and expansion data also were able to be collected. The circulation micropump is rated to 5000 psi, with a pressure head of 75 psi and maximum temperature of 250° C. The feed pump (Eldex Laboratories Inc. 1020 BBB-4) is used to pump the organic solvent into the system. $CO_2$ is pressurized by a syringe pump (ISCO Model 260D), which is insulated with a circulating water bath (Isotemp 30165 Fisher Scientific) to keep the $CO_2$ at constant temperature. The system pressure is recorded by an in-situ pressure transducer with a maximum pressure limit of 30000 psi and a Heise digital pressure indicator.

The viscometer is a cylindrical cell with a piston inside it. Fluid is trapped in the annulus between piston and cylindrical cell wall. Two magnetic coils inside the sensor body vibrate the piston over a fixed distance, forcing the fluid to flow through the annular space between piston and chamber. The time required for the piston to complete a two-way cycle is directly related to the viscosity of the fluid. The viscometer sensor is capable of measuring viscosities from 0.02 to 10,000 cP with maximum operating pressure of 20,000 psi (1379 bar) and operating temperature ranging from −40 to +190° C.

The viscometer is oriented at a 45° angle so that any gas bubble trapped inside can be purged easily. According to manufacturer's specifications, the accuracy of the viscosity measurement is ±1% of the measured viscosity. The viscometer temperature is measured by a temperature sensor located at the bottom of the viscometer, with an accuracy of ±0.01° C. The raw viscosity data from the instrument reading were adjusted by temperature and pressure with a program provided by manufacture.

Prior to viscosity measurements, the volume expansion of organic mixtures with various phosphorous ligands dissolved in toluene was performed in Jerguson viewcell. $CO_2$ was gradually added to the mixture and after the temperature and pressure stabilized the volume of the mixture was recorded at each desired temperature and pressure until the highest $CO_2$ pressure is arrived at which the mixtures become cloudy. This highest $CO_2$ pressure is called cloud point pressure, which is the maximum $CO_2$ pressure that the organic mixtures can tolerate while remaining homogeneous. The cloud points are different for each specific mixture with different concentrations of phosphorous ligands. During the expansion and cloud point measurements, the viscometer was bypassed to prevent the piston from scratch by any particles formed when the cloud point is approached.

Figure 13:
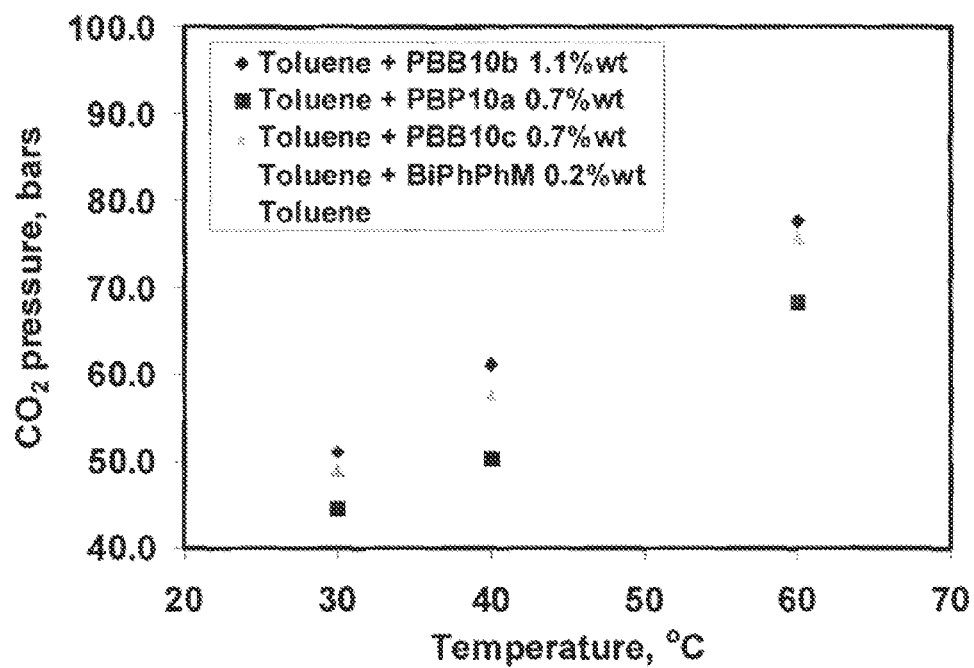
FIG. 13 shows the cloud points of different mixtures at different temperatures.

Of the systems that have been tested in this study shown in FIG. 13, pure toluene and the mixture of toluene and BiPhPhM ligand are miscible with $CO_2$ and do not display cloud points in the pressure and temperature ranges tested. Polymer supported ligands PBB10b, PBP10a and PBB10c precipitate out at the highest $CO_2$ pressures shown in the figure. The cloud point pressure increases with increasing temperature.

The cloud point measurements essentially provide the operating temperature and pressure ranges under which the polymer supported catalysts would remain in solution upon $CO_2$ addition and thereby facilitate homogeneous catalysis.

Figure 14:
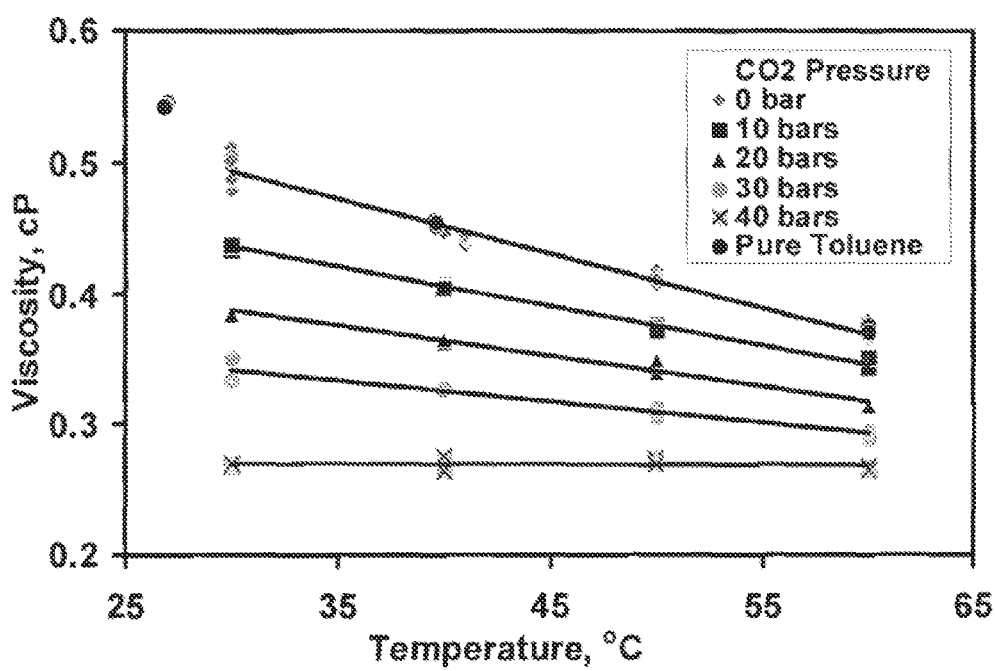
FIG. 14 shows the viscosities of toluene plus PBBc 0.7% at different temperatures and $CO_2$ pressures.

FIG. 14 shows the viscosities measured for the mixture of toluene and PBB10c at a concentration of 0.7% by weight at four temperatures and five $CO_2$ pressures below the cloud point pressure. The viscosities decrease with increasing temperature at the same $CO_2$ pressure and with increasing $CO_2$ pressure at the same temperature. Viscosities decrease 50% and 30% respectively by adding $CO_2$ up to 40 bars at temperature 30° C. and 60° C. Negligible change in viscosity was observed with temperature at $CO_2$ pressure of 40 bars. $CO_2$ addition to the hydroformylation reaction mixture not only improves the linear aldehyde selectivity (demonstrated in Subramaniam et al., U.S. Pat. No. 7,365,234, which is incorporated by reference) but also decreases viscosity, thus providing an ability to tune the membrane flux.

Figure 15:
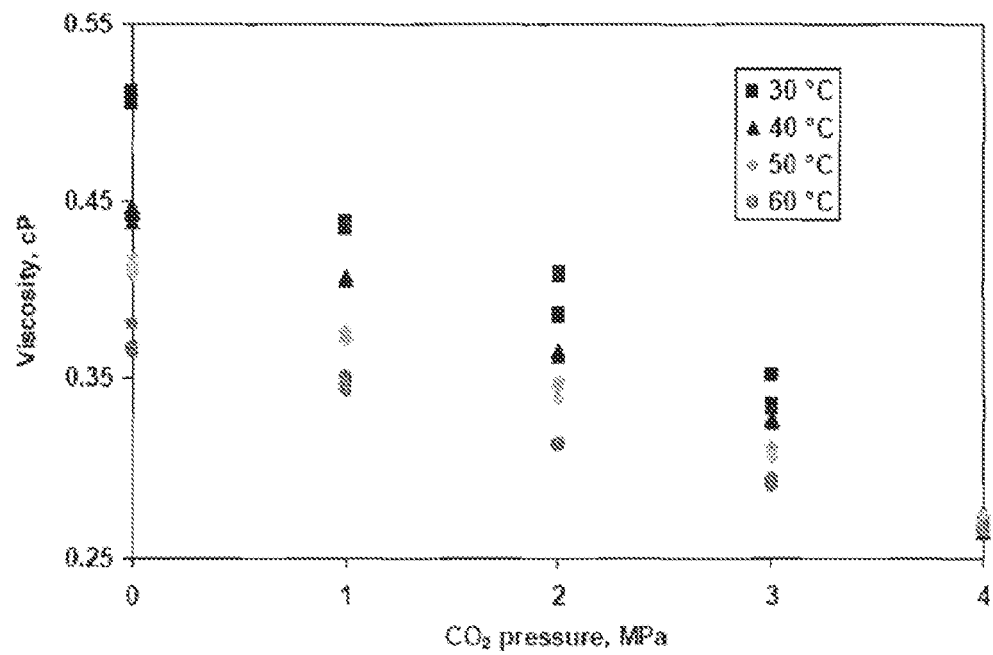
FIG. 15 shows the variation of viscosities of toluene+0.7 wt % PBB10c mixture with $CO_2$ pressures at different temperatures.

Another evidence that 2-3 times higher pure toluene flux was observed for $CO_2$ than nitrogen of the identical pressure 55 bars at the same temperature proved that $CO_2$ addition can facilitate solvent permeation. The relation of viscosity and $CO_2$ pressure at different temperature for the mixture toluene plus PBB10c at a concentration of 0.7% by weight is plotted in FIG. 15. Clearly, the viscosity drops when increasing $CO_2$ pressure at all temperatures. At lower temperature, the viscosity decreases more rapidly than that at higher temperature. This observation is consistent with the fact that at low temperature the mixture has higher volume expansion (higher $CO_2$ solubility) than at high temperature under the same $CO_2$ pressure.

Figure 16:
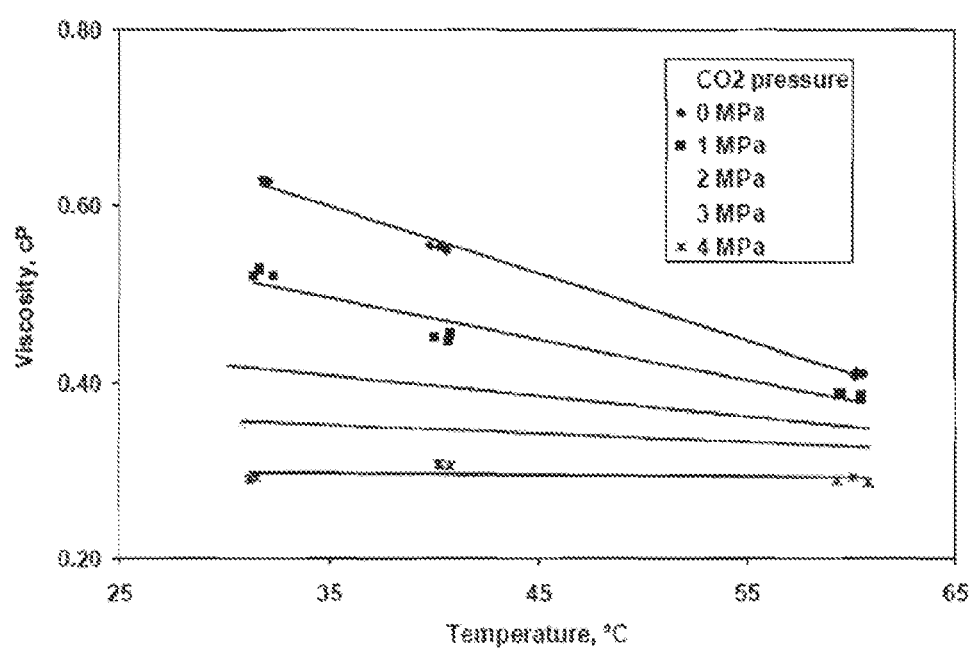
FIG. 16 shows the variation of viscosities with temperature for toluene+1.8 wt % PBB10c mixtures at different $CO_2$ pressures.
Figure 17:
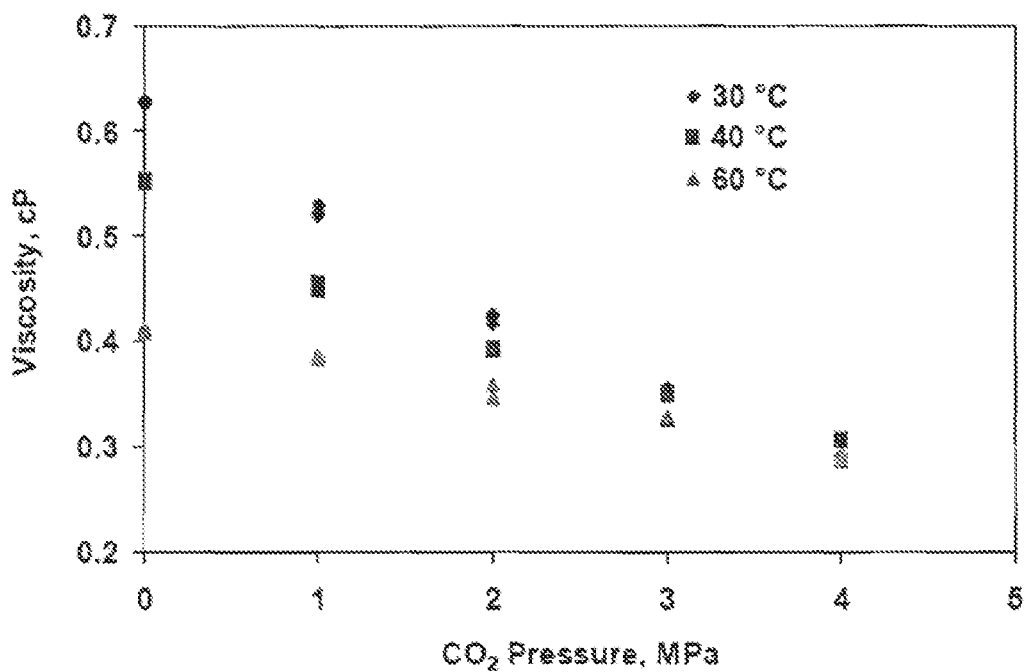
FIG. 17 shows the variation of viscosities of toluene+1.8 wt % PBB10c mixtures with $CO_2$ pressures at different temperatures.

The same trends were observed for the change in viscosities with temperature and $CO_2$ pressure in FIG. 16 and FIG. 17, respectively, for a system containing higher concentrations of polymer bound ligands (1.8% by weight).

Figure 18:
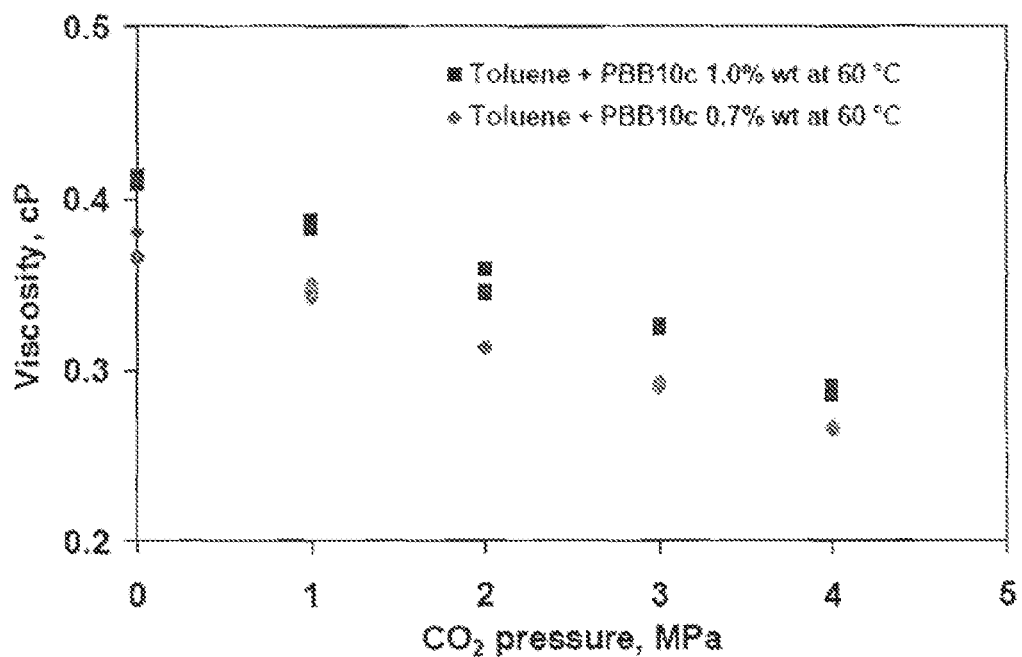
FIG. 18 shows the viscosities versus $CO_2$ pressures of toluene+1.8 wt % PBB10c mixture at 60° C.

FIG. 18 shows the change in viscosity change with $CO_2$ pressure at 60° C. for different polymer concentrations. At the same temperature and $CO_2$ pressure, the viscosity increases with increasing polymer concentration. The degree of reduction in viscosity upon $CO_2$ addition is similar for both low and high polymer concentration mixtures.

The dissolution of $CO_2$ in organic solvents reduces the viscosities and increases the diffusivities of the organic solvents. Compared with other inert gas such as nitrogen, $CO_2$ could not only serve as a pressurizing gas, but also as a reagent to tune the viscosities of the organic mixtures. Viscosity measurements of organic mixtures with various phosphorus ligands dissolved in toluene at different $CO_2$ pressures and temperatures provide the evidence for the $CO_2$ tuning ability.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A process for the separation of a catalyst composition from a reaction mixture comprising:
   providing the reaction mixture comprising a reactant, a substrate, an optional solvent, and the catalyst composition comprising a polymer functionalized with a multidentate ligand for binding a transition metal containing compound to form a transition metal complex, wherein said functionalized polymer has a number average molecular weight of about 5,000 to 30,000 g/mol and a polydispersity index of about 1.0 to 2.0, and a transition metal complexed to said multidentate ligand, and wherein said substrate and said catalyst composition are in a liquid phase;
   adding a compressed gas into said reaction mixture to provide pressure for nanofiltration of said catalyst composition such that the compressed gas does not cause precipitation of the catalyst composition and
   filtering said liquid phase through a filter to form a retentate composition and a permeate composition, and wherein said retentate composition retains said catalyst composition.

2. The process of claim 1 wherein said reactant is a reactant gas selected from the group consisting of CO, $O_2$, $H_2$, or a $H_2$/CO syngas.

3. The process of claim 2 wherein said reactant gas is also said compressed gas.

4. The process of claim 1 wherein said compressed gas is an inert gas.

5. The process of claim 4 wherein said inert gas is selected from the group consisting of nitrogen, carbon dioxide, xenon, $SF_6$, argon, or helium.

6. The process of claim 1 wherein said compressed gas is compressed carbon dioxide, and wherein said liquid phase is volumetrically expanded with said compressed carbon dioxide, and wherein the viscosity of said liquid phase is reduced compared to a liquid phase without said compressed carbon dioxide.

7. The process of claim 1 wherein said reaction mixture is a hydrogenation reaction mixture, a hydroformylation reaction mixture, an oxidation reaction mixture, or a carbonylation reaction mixture, or a combination thereof.

8. The process of claim 1 wherein said substrate comprises an olefin substrate, said reactant comprises a $H_2$/CO syngas, and said catalyst composition comprises a hydroformylation catalyst in said liquid phase.

9. The process of claim 8 wherein the said olefin substrate is a higher olefin having more than 5 carbons, and wherein said olefin substrate is selected from the group consisting of a linear olefin, branched olefin, an olefin having a terminal double bond, and an olefin having an internal double bond.

10. The process of claim 8 wherein said hydroformylation catalyst composition comprises a rhodium containing compound complexed to a polymer functionalized with a phosphorous-containing ligand.

11. The process of claim 8 wherein said reaction mixture further comprises an organic solvent.

12. The process of claim 11 wherein said organic solvent is acetone, toluene, tetrahydrofuran, or dichloromethane.

13. The process of claim 11 wherein said organic solvent is a mixture of said olefin substrate and an aldehyde that is the product of the hydroformylation reaction.

14. The process of claim 1 wherein said compressed gas has a volume fraction in the liquid phase between 10% and 90%.

15. The process of claim 1 wherein said compressed gas is dense carbon dioxide.

16. The process of claim 1 wherein said substrate is an oxidizable substrate, and wherein said compressed gas comprises a gas selected from the group consisting of oxygen, air, or a combination thereof.

17. The process of claim 1 wherein said substrate is a hydrogenation substrate, and wherein said compressed gas comprises $H_2$.

18. The process of claim 1 wherein said substrate is a carbonylation substrate, and wherein said compressed gas comprises CO.

19. The process of claim 1 wherein said filtering step is conducted in a batch, semi-continuous, or continuous manner.

20. The process of claim 1 wherein said filtering step comprises filtering said liquid phase through a polyimide membrane.

21. The process of claim 20 wherein said filtering step comprises filtering said liquid phase through a filter having a molecular weight cut-off range of 100 to 1000 g/mol based on 90% rejection of the solute.

22. The process of claim 1 wherein said permeate composition has a concentration of the transition metal less than 100 ppb.

23. The process according to claim 1 wherein the concentration of said transition metal in the liquid phase of said reaction mixture is between 100 ppb to 2000 ppm.

24. The process of claim 1 wherein said transition metal is selected from the group consisting of rhodium, cobalt, iridium, ruthenium, nickel, palladium, and platinum.

25. The process of claim 1 wherein said functionalized polymer is selected from the group consisting of a copolymer of polystyrene or polyethylene glycol, and wherein said ligand comprises a phosphine, phosphinane, phosphinine, phosphinite, phosphite, or phosphonite.

26. The process of claim 1 wherein said functionalized polymer comprises polystyrene having at least one moiety selected from the group consisting of amino, epoxy, carboxylic acid, carboxylic ester, ortho ester, anhydride, carbon-carbon double bond, phosphine, phosphite, and pyridyl.

27. The process of claim 1 wherein said functionalized polymer comprises polystyrene functionalized with said multidentate ligand selected from the group consisting of ligand comprises a phosphine, phosphinane, phosphinine, phosphinite, phosphite, and phosphonite.

28. The process of claim 1 wherein the number average molecular weight of said functionalized polymer is about 9,000 to 12,000 g/mol.

29. The process of claim 1 wherein the polydispersity index of said functionalized polymer is from about 1.0 to 1.5.

30. The process of claim 1 wherein said transition metal is selected from the group consisting of rhodium, cobalt, iridium, ruthenium, nickel, palladium, and platinum.

31. The process of claim 1 wherein said functionalized polymer comprises polystyrene-co-6,6'-(3,3'-di-tert-butyl-5,5'-divinylbiphenyl-2,2' diyl)bis(oxy)didibenzo[1,3,2]dioxaphosphepine.

32. The process of claim 1 wherein said substrate is a ketone, aldehyde, enone, enal, olefin, alkyne, alcohol, oxidizable substrate, or mixtures thereof.

33. The process of claim 1 wherein said filter has a pore size less than 50 angstroms.

34. The process of claim 1 wherein said permeate composition has a concentration of the transition metal which is less than 50 ppb.

35. The process of claim 1 wherein said permeate composition has a concentration of the transition metal which is less than 30 ppb.

36. The process of claim 20 wherein said filtering step comprises filtering said liquid phase through a filter having a molecular weight cut-off range of 150 to 600 g/mol based on 90% rejection of the solute.

37. The process of claim 20 wherein said filtering step comprises filtering said liquid phase through a filter having a molecular weight cut-off range of 200 to 500 g/mol based on 90% rejection of the solute.

* * * * *